(12) United States Patent
Huang et al.

(10) Patent No.: US 8,946,201 B2
(45) Date of Patent: Feb. 3, 2015

(54) METHODS FOR INHIBITING TGF-β

(75) Inventors: Shuan Shian Huang, St. Louis, MO (US); Jung San Huang, St. Louis, MO (US)

(73) Assignees: Saint Louis University, St. Louis, MO (US); Auxagen, Inc., St. Louis, MO (US)

( * ) Notice: Subject to any disclaimer, the term of this patent is extended or adjusted under 35 U.S.C. 154(b) by 328 days.

(21) Appl. No.: 12/199,459

(22) Filed: Aug. 27, 2008

(65) Prior Publication Data

US 2009/0062247 A1    Mar. 5, 2009

Related U.S. Application Data

(60) Provisional application No. 60/968,097, filed on Aug. 27, 2007.

(51) Int. Cl.
  *A01N 43/00*  (2006.01)
  *A61K 31/33*  (2006.01)
  *A01N 45/00*  (2006.01)
  *A61K 31/56*  (2006.01)

(52) U.S. Cl.
  CPC ..................... *A61K 31/56* (2013.01)
  USPC .......................... 514/183; 514/171

(58) Field of Classification Search
  USPC .................................. 514/183, 171
  See application file for complete search history.

(56) References Cited

U.S. PATENT DOCUMENTS

| | | | |
|---|---|---|---|
| 4,058,620 A | 11/1977 | Westley | |
| 4,179,337 A | 12/1979 | Davis et al. | |
| 4,423,037 A | 12/1983 | Rosenblatt et al. | |
| 4,456,596 A | 6/1984 | Schafer | |
| 4,666,907 A | 5/1987 | Fortin et al. | |
| 4,959,314 A | 9/1990 | Mark et al. | |
| 5,118,791 A | 6/1992 | Burnier et al. | |
| 5,147,854 A | 9/1992 | Newman | |
| 5,444,151 A | 8/1995 | Vassbotn et al. | |
| 5,571,714 A | 11/1996 | Dasch et al. | |
| 5,616,561 A | 4/1997 | Barcellos-Hoff | |
| 5,624,938 A | 4/1997 | Pernis | |
| 5,654,270 A | 8/1997 | Ruoslahti et al. | |
| 5,693,607 A * | 12/1997 | Segarini et al. .......... | 514/2 |
| 5,824,297 A | 10/1998 | Iwata et al. | |
| 5,981,606 A | 11/1999 | Martin | |
| 5,981,621 A | 11/1999 | Clark et al. | |
| 6,068,845 A | 5/2000 | Aoki et al. | |
| 6,075,005 A | 6/2000 | Lurie | |
| 6,316,258 B1 | 11/2001 | Noble et al. | |
| 6,337,320 B1 | 1/2002 | Hersh et al. | |
| 6,500,920 B1 | 12/2002 | Haung | |
| 6,649,588 B1 | 11/2003 | Tabibzadeh et al. | |
| 6,806,358 B2 | 10/2004 | Bier et al. | |
| 6,838,076 B2 | 1/2005 | Patton et al. | |
| 6,906,026 B1 | 6/2005 | Noble et al. | |
| 7,057,013 B1 | 6/2006 | Ezquerro et al. | |
| 7,723,473 B2 | 5/2010 | Huang | |
| 7,741,283 B2 | 6/2010 | Huang | |
| 7,973,022 B2 | 7/2011 | Murthy | |
| 8,110,655 B2 | 2/2012 | Huang et al. | |
| 2003/0059447 A1* | 3/2003 | Lambers ...................... | 424/401 |
| 2004/0116407 A1 | 6/2004 | Borisy | |
| 2004/0229791 A1 | 11/2004 | Huang | |
| 2005/0250801 A1 | 11/2005 | Shailubhai et al. | |
| 2006/0153794 A1 | 7/2006 | Hibino et al. | |
| 2006/0233708 A1 | 10/2006 | Huang | |
| 2007/0053957 A1 | 3/2007 | Kennedy et al. | |
| 2007/0203097 A1 | 8/2007 | Murthy | |
| 2008/0194690 A1 | 8/2008 | Bastin et al. | |
| 2008/0319010 A1 | 12/2008 | Kastan et al. | |
| 2010/0075923 A1 | 3/2010 | Huang et al. | |
| 2011/0008248 A1 | 1/2011 | Huang | |

FOREIGN PATENT DOCUMENTS

| | | |
|---|---|---|
| EP | 0433225 B1 | 4/1999 |
| EP | 1132403 B1 | 5/2006 |
| GB | 2 305 123 A1 | 4/1997 |
| WO | 93/25225 A1 | 12/1993 |
| WO | 97/08196 A1 | 3/1997 |
| WO | 98/04245 A1 | 2/1998 |
| WO | 0031135 A1 | 6/2000 |
| WO | 03093293 A2 | 11/2003 |
| WO | 2004080478 A1 | 9/2004 |
| WO | 2005049009 A1 | 6/2005 |
| WO | 2006138048 A2 | 12/2006 |
| WO | 2009029656 | 3/2009 |
| WO | 2009114700 A2 | 9/2009 |
| WO | 2010033507 | 3/2010 |

OTHER PUBLICATIONS

Grainger et. al. (Journal of Lipid Research (1997) 38:2344-2352).*
Grainger, et al., "Transforming Growth Factor Beta is Sequestered into an Inactive Pool by Lipoproteins," J. Lipid Res., 1997; 38(11):2344-52; abstract p. 2344.
Valencia, et al., "7-Dehydrocholesterol Enhances Untraviolet A-Induced Oxidative Stress in Keratinocyles: Roles in NADPH Oxidase, Mitochondria and Lipid Rafts," Free Radic Biol Med., 2006; 41(11):1704-1718.
Office Action dated May 29, 2012 for related Chinese Patent Application No. 200980136369.2; 5 pages.
Statements of the Grounds for Appeal dated Mar. 8, 2010 for related European Patent Application No. 03728390.0, 36 pages.

(Continued)

*Primary Examiner* — Marcos Sznaidman

(57) ABSTRACT

The present invention provides methods for inhibiting or blocking TGF-β activity in cells and/or tissues expressing TGF-β comprising, contacting cells and/or tissues expressing TGF-β with an amount of cholesterol or cholesterol derivative effective to inhibit the activity of TGF-β. The present invention further provides a method for treating a condition associated with overactivity of TGF-β or negative regulation in normal physiology by TGF-β in a subject in need of treatment, comprising contacting cells and/or tissue overexpressing TGF-β in the subject with an amount of cholesterol or cholesterol derivative effective to inhibit activity of TGF-β thereby treating the condition. In a preferred embodiment, the cholesterol derivative is oxidized 7-DHC.

8 Claims, 17 Drawing Sheets

(56) References Cited

OTHER PUBLICATIONS

Summons to Oral Proceedings dated Jul. 17, 2009 for related European Patent Application No. 03728390.0, 9 pages.
Written Submission dated Aug. 27, 2009 for related European Patent Application No. 03728390.0, 33 pages.
Notice of Allowance for U.S. Appl. No. 11/432,125, dated Dec. 22, 2009, 5 pages.
Notice of Allowance for U.S. Appl. No. 11/939,126, dated Sep. 23, 2011, 8 pages.
Office action for Canadian Patent Application No. 2,484,994, dated Aug. 3, 2011, 3 pages.
Office action for Canadian Patent Application No. 2,699,454, dated May 13, 2011, 3 pages.
Office action for European Patent Application No. 03728390.0, dated Jan. 18, 2008, 9 pages.
Office action for U.S. Appl. No. 09/095,637, dated Aug. 30, 1999, 7 pages.
Office action for U.S. Appl. No. 09/095,637, dated May 23, 2000, 16 pages.
Office action for U.S. Appl. No. 09/095,637, dated Apr. 4, 2001, 11 pages.
Office action for U.S. Appl. No. 09/095,637, dated Aug. 21, 2001, 5 pages.
Office action for U.S. Appl. No. 09/095,637, dated Dec. 6, 2000, 6 pages.
Office action for U.S. Appl. No. 09/095,637, dated Nov. 28, 2001, 7 pages.
Office action for U.S. Appl. No. 10/135,946, dated Jan. 9, 2006, 12 pages.
Office action for U.S. Appl. No. 10/135,946, dated Jun. 21, 2005, 16 pages.
Office action for U.S. Appl. No. 10/748,703, dated Nov. 1, 2007, 6 pages.
Office action for U.S. Appl. No. 10/966,371, dated Dec. 15, 2008, 10 pages.
Office action for U.S. Appl. No. 10/966,371, dated Jan. 4, 2008, 8 pages.
Office action for U.S. Appl. No. 10/966,371, dated Oct. 15, 2008, 6 pages.
Office action for U.S. Appl. No. 11/432,125, dated Aug. 7, 2008, 15 pages.
Office action for U.S. Appl. No. 11/432,125, dated Jan. 13, 2009, 12 pages.
Office action for U.S. Appl. No. 11/432,125, dated Jun. 24, 2009, 10 pages.
Office action for U.S. Appl. No. 11/939,126, dated Jan. 7, 2011, 5 pages.
Office action for U.S. Appl. No. 11/939,126, dated May 14, 2010, 7 pages.
Office action for U.S. Appl. No. 12/199,459, dated Aug. 19, 2010, 10 pages.
Office action for U.S. Appl. No. 12/199,459, dated Jan. 26, 2011, 16 pages.
Office action for U.S. Appl. No. 12/560,136, dated Jan. 30, 2012, 7 pages.
O'Grady et al., Purification of a New Type High Molecular Weight Receptor (Type V Receptor) of Transforming Growth Factor β (TGF-β) from Bovine Liver, J. Biol. Chem. 266:8583-8589 (1991).
O'Kane, et. al., Transforming Growth Factors Bs and Wound Healing, Elsevier Science Ltd., 1997, pp. 63-78.
Postlethwaite et al., Identification of a chemotactic epitope in human transforming growth factor-beta 1 spanning amino acid residues 368-374., J Cell Physiol. Sep. 1995; 164(3):587-92.
Qian et al. Identification of a structural domain that distinguishes the actions of the type 1 and 2 isoforms of transforming growth factor beta on endothelial cells. Proc Natl Acad Sci., Jul. 15, 1992;89(14):6290-4.
Qian et al., "Binding affinity of transforming growth factor-beta for its type 11 receptor is determined by the C-terminal region of the molecule." J Biol Chem. Nov. 29, 1996; 271(48):30656-62.
Qian et al., "Characterization of mutated transforming growth factor beta- s which possess unique biological properties." Biochemistry. Oct. 11, 1994; 33(40): 12298-304.
Qian et al., "Distinct functional domains of TGF-beta bind receptors on endothelial cells." Growth Factors. 1999; 17 (1):63-73.
Ricort et al., "Insulin-like Growth Factor-binding Protein-3 Activates a Phosphotyrosine Phosphatase," J. Biol. Chem., May 31, 2022, vol. 277, No. 22, pp. 19448-19454.
Rocha et al., "Insulin-like Growth Factor Binding Protein-3 and Insulin Receptor Substrate-1 in Breast Cancer: Correlation with Clinical Parameters and Disease-free Survival," Clin. Can. Res., Jan. 1997, vol. 3, pp. 103-109.
Rudinger, J. "Characteristics of the amino acids as components of a peptide hormone sequence," Peptide Hormones, Jun. 1976, University Park Press.
Runyan, et al., TGF-beta receptor-binding proteins: complex interactions. Cellular Signalling, (2006) 18, 2077-2088.
Schlunegger et al., "Refined crystal structure of human transforming growth factor beta 2 at 1.95 A resolution." J Mol Biol. May 20, 1993; 231(2):445-58.
Schlunegger et al., An unusual feature revealed by the crystal structure at 2.2A resolution of human transforming growth factor-β2, Nature, 358:430-434 (1992).
Shah, et al., Neutralising Antibody to TGF-B1,2 Reduces Cutaneous Scarring in Adult Rodents, Journal of Cell Science, 1994, pp. 1137-1157.
Shah, et. al., "Neutralisation of TGF-β, and TRG-β2 or Exogenous Addition of TGF-β3 to Cutaneous Rat Wounds Reduces Scarring," Journal of Cell Science, Mar. 1995, 108 (Pt 3):985-1002.
Supplementary European Search Report for European Patent Application No. 03728390.0, dated Oct. 4, 2007, 3 pages.
Tanaka et al., " Insulin Receptor Substrate 1 Overexpression in Human Hepatocellular Carcinoma Cells Prevents Transforming Growth Factor β1-induced Apoptosis," Cancer Res., Aug. 1, 1996, 56(15), pp. 3391-3394.
Van Scott et al., "Detection of Radiation Effects on Hair Roots of the Human Scalp," Journal of Investigative Dermatology, (1957), 29(3), pp. 205-212.
Written Opinion for PCT Application No. PCT/US09/56994, mailed Dec. 9, 2009, 4 pages.
Written Opinion for PCT Application No. PCT/US2008/74446, mailed Nov. 26, 2008, 5 pages.
Xia, et al., "Effects of Keratinocyte Growth Factor-2 (KGF-2) on Wound Healing in an Ischaemia-Impaired Rabbit Ear Model and on Scar Formation," Journal of Pathology, 1999, pp. 431-438.
Zambruno, et al., "Transforming Growth Factor-β1 Modulates β1 and β5 Integrin Receptors and Induces the de novo Expression of the αvβ6 Heterodimer in Normal Human Keratinocytes," Implications for Wound Healing, May 1995, pp. 853-865, The Rockefeller University Press.
Web, et al., Transforming Growth Factor β Isoform 2-specific High Affinity Binding to Native α2-Macroglobulin, J. Biological Chem., 1994, pp. 30402-30406, vol. 269, No. 48.
Office action for Canadian Application No. 2,484,994, dated Jun. 7, 2010, 4 pages.
Minutes of the Oral Proceedings dated Oct. 29, 2009 for related European Patent Application No. 03728390.0, 25 pages.
Negre-Aminou, P. et al., "Inhibition of proliferation of human smooth muscle cells by various HMG-CoA reductase inhibitors; comparison with other human cell types," Biochimica et Biophysica Acta, 1997, pp. 259-268, vol. 1345.
Office Action dated Jul. 17, 2012 for related U.S. Appl. No. 12/560,136; 11 pages.
Notice of Allowance dated Mar. 12, 2013 for related U.S. Appl. No. 12/560,136; 10 pages.
Kirchhausen, T. et al., "Use of Dynasore, the Small Molecule Inhibitor of Dynamin, in the Regulation of Endocytosis," Methods in Enzymology, 2008, vol. 438, pp. 77-93.
Office action dated Jan. 22, 2013 for related Canadian Patent Application No. 2,484,994; 2 pages.

(56) References Cited

OTHER PUBLICATIONS

Office action dated Feb. 17, 2013 for related Chinese Patent Application No. 200980136369.2; 4 pages (English translation only).
Office action dated Nov. 29, 2012 for related U.S. Appl. No. 12/560,136; 9 pages.
Amendt, et al., "Resistance of Keratinocytes to TGFB-Mediated Growth Restriction and Apoptosis Induction Accelerates Re-epithelialization in Skin Wounds," Journal of Cell Science, 2002, pp. 2189-2198.
Ashcroft, et al., "Mice Lacking Smad3 Show Accelerated Wound Healing and an Impaired Local Inflammatory Response," Nature Cell Biology, Sep. 1999, pp. 260-266.
Bowie et al., "Deciphering the message in protein sequences: tolerance to amino acid substitutions." Science, Mar. 16, 1990, vol. 247 (4948) 1306-10.
Burmester et al., "Characterization of distinct functional domains of transforming growth factor beta." Proc Natl Acad Sci USA. Sep. 15, 1993; 90(18):8628-32.
Burmester et al., "Mutational analysis of a transforming growth factor-beta receptor binding site." Growth Factors. 1998, 15(3):23142.
Chan, et al., "Accelerated Skin Wound Healing in Plasminogen Activator Inhibitor-1-Deficient Mice," American Journal of Pathology, Nov. 2001, pp. 1681-1688.
Chen et al: "Inhibitors of clathrin-dependent endocytosis enhance TGF signaling and responses", Journal of Cell Science, vol. 122, No. 11, May 20, 2009, pp. 1863-1871.
Chen, et al., "Cholesterol suppresses cellular TGF-beta responsiveness: implications in atherogenesis," Journal of Cell Science, (2007), 120, pp. 3509-3621.
Chow et al., "Reduction in Rate of Growth of Hair in Mice as an Indicator of Exposure to Chronic Low Dosage Ionizing Radiation," Nature, Aug. 22, 1964, 203, No. 4947, pp. 847-848.
Daopin et al., "Crystal structure of transforming growth factor-beta 2: an unusual fold for the superfamily." Science. Jul. 17, 1992; 257(5068):369-73.
Darlak et al., "Assessment of biological activity of synthetic fragments of transforming growth factor-alpha." J Cell Biochem. Apr. 1988; 36(4):341-52.
Das, "Free radicals, cytokines and nitric oxide in cardiac failure and myocardial infarction," Molecular and Cellular Biochemistry, 2000, 215: 145-152.
Demetriou et al., "Fetuin/α2-HS Glycoprotein Is a Transforming Growth Factor-β Type II Receptor Mimic and Cytokine Antagonist," J. Biol. Chem., May 31, 1996, vol. 271, No. 22, pp. 12755-12761.
Derynck et al., Human transforming growth factor-f complementary DNA sequence and expression in normal and transformed cells, Nature 316:701-705 (1985).
Di Guglielmo et al., "Distinct 1-14 endocytic pathways regulate TGF-[beta] receptor signalling and turnover", Nature Cell Biology, vol. 5, No. 5, Apr. 28, 2003, pp. 410-421.
Extended European Search Report for European Patent Application No. 08798785.5, dated Jul. 27, 2010, 7 pages.
Extended European Search Report for European Patent Application No. 09815064.2, dated Jan. 19, 2012, 8 pages.
Hinck et al., Transforming Growth Factor β1: Three-Dimensional Structure in Solution and Comparison with the X-ray Structure of Transforming Growth Factor β 2, Biochemistry 35:8517-8534 (1996).
Huang et al., A Pentacosapeptide (CKS-25) Homologous to Retroviral Envelope Proteins Possesses a Transforming Growth Factor-f Activity, J. Biol. Chem. 273:4815-4818 (1998).
Huang et al., Activated Thyroglobulin Possesses a Transforming Growth Factor-βActivity, J. Biol. Chem. 273:26036-26041 (1998).
Huang et al., Amyloid β-Peptide Possesses a Transforming Growth Factor-β Activity, J. Biol. Chem. 273:27640-17644 (1998).
Huang, et al., "An Active Site of Transforming Growth Factor B, for Growth Inhibition and Stimulation," The Journal of Biological Chemistry, Sep. 24, 1999, pp. 27754-27758.
Huang, et al., "Synthetic TGF-B Antagonist Accelerates Wound Healing and Reduces Scarring," FASEB Journal, pp. 1-2, Aug. 2002.
Huang, et al., "Synthetic TGF-B Antagonistic Accelerates Wound Healing and Reduces Scarring," FASEB Journal, Aug. 2002; 16(10):1269-70. Epub Jun. 21, 2002.
Huang, et al., "Transforming Growth Factor B Peptide Antagonists and Their Conversion to Partial Agonists," The Journal of Biological Chemistry, Oct. 24, 1997, pp. 27155-27159.
Huynh et al., "A Possible Role for Insulin-like Growth Factor-binding Protein-3 Autocrine/Paracrine Loops in Controlling Hepatocellular Carcinoma Cell Proliferation," Cell Growth & Diff., Mar. 2002, vol. 13, pp. 115-122.
Inoue, M.D. et al., TGF-132 is specifically expressed in human dermal papilla cells and modulates hair folliculogenesis, Journal of Cellular and Molecular Medicine, dated Oct. 16, 2008 (29 pages).
International Search Report for PCT Application No. PCT/US09/56994, mailed Dec. 9, 2009, 2 pages.
International Search Report for PCT Application No. PCT/US2003/11437, mailed Feb. 10, 2005, 1 page.
International Search Report for PCT Application No. PCT/US2008/74446, mailed Nov. 26, 2008, 2 pages.
Juengst, "What Next for Human Gene Therapy?," BMJ, Jun. 28, 2003, 326(7404), pp. 1410-1411.
Kingsley DM. The TGF-beta superfamily: new members, new receptors, and new genetic tests of function in different organisms. Genes Dev. Jan. 1994;8(2):133-46.
Laiho et al., Concomitant Loss of Transforming Growth Factor (TGF)-β Receptor Types I and II in TGF-β-resistant Cell Mutants Implicates Both Receptor Types in Signal Transduction, J. Biol. Chem. 265:18518-18524 (1990).
Leal et al., "The Type V Transforming Growth Factor β Receptor is The Putative Insulin-like Growth Factor-binding Protein 3 Receptor," Aug. 15, 1997, vol. 272, No. 33, pp. 20572-20576.
Limbird, L.L. "Identification of Receptors Using Direct Radioligand Binding Techniques," Chapter 3 in Cell Surface Receptors: A Short Course on Theory and Methods, 2nd ed., Kluwer Academic Publishers, Massachusetts, 1996, pp. 61-65.
Ling, T-Y, et al., "Fatty acids modulate transforming growth factor-beta activity and plasma clearance," The FASEB Journal, Jun. 3, 2003.
Liu et al., "Function of the Type V Transforming Growth Factor β Receptor in Transforming Growth Factor β-induced Growth Inhibition of Mink Lung Epithelial Cells," J. Biol. Chem., Jul. 25, 1997, vol. 272, No. 30, pp. 18891-18895.
Liu, et al., "Identification of the High Affinity Binding Site in Transforming Growth Factor-B Involved in Complex Formation with a2-Macroglobulin," the Journal of Biological Chemistry, Dec. 7, 2001, pp. 46212-46218.
Macia, et al., "Dynasore, a Cell-Permeable Inhibitor of Dynamin," Dev. Cell. (2006) , 10, pp. 839-850.
Madisen et al., Transforming Growth Factor-β2: eDNA Cloning and Sequence Analysis, DNA7:1-8 (1988).
Mcdonald et al. A structural superfamily of growth factors containing a cystine knot motif. Cell. May 1993, 7;73 (3):421-4.
Miller et al. GenBank Database Accession No. M32745. National Center for Biotechnology Information, Bethesda, MD. Apr. 27, 1993.
Mittl et al. The crystal structure of TGF-beta 3 and comparison to TGF-beta 2: implications for receptor binding. Protein Science, (Jul. 1996) 5 (7) 1261-71.
Mosley et al., "Neuroinflammation, Oxidative Stress and the Pathogenesis of Parkinson's Disease" Clin Neurosci Res (2006) vol. 6 No. 5 pp. 261-281.
Mousavi et al., "Clathrin-dependent endocytosis", Biochemical Journal, vol. 377, No. I, Jan. 1, 2004, pp. 1-16.
Mustoe, et al., "Growth Factor-induced Acceleration of Tissue Repair Through Direct and Inductive Activities in a Rabbit Dermal Ulcer Model," Feb. 1991, pp. 694-703.
Ngo et al., "Computational Complexity, Protein Structure, Prediction, and the Levinthal Paradox," The Protein Folding Problem and Tertiary Structure Prediction, Merz and Le Grand (Eds), Aug. 1994, Springer Verlag, pp. 433 and 492-495.
Notice of Allowance for Canadian Application No. 2,699,454, dated Nov. 28, 2011, 1 page.
Notice of Allowance for U.S. Appl. No. 09/095,637, dated Jun. 10, 2002, 4 pages.
Notice of Allowance for U.S. Appl. No. 10/966,371, dated Jul. 14, 2009, 6 pages.

* cited by examiner

US 8,946,201 B2

METHODS FOR INHIBITING TGF-β

RELATED APPLICATION

This application claims the benefit of U.S. Provisional Application No. 60/968,097, filed on Aug. 27, 2007. The entire teachings of the above application are incorporated herein by reference.

GOVERNMENT SUPPORT

This invention was made with government support under grant number AR052578 awarded by National Institutes of Health. The government has certain rights in the invention.

BACKGROUND OF THE INVENTION

Transforming growth factor-beta (TGF-β), which is a family of 25-kDa dimeric proteins and has three members TGF-$β_{1-3}$ in mammalian species, is a pleiotropic cytokine that regulates multiple biological processes, including extracellular matrix synthesis, cell proliferation, apoptosis and differentiation of many cell types and immune response. Many cell types synthesize and secrete TGF-β, and almost all of them express specific receptors for TGF-β.

The cell biological activities of TGF-β are well documented. TGF-β is a bifunctional growth regulator; it inhibits cell growth of most cell types including epithelial cells, endothelial cells and T cells but stimulates growth of mesenchymal cells such as fibroblasts and chondrocytes. The growth inhibitory activity of TGF-β toward T cells has been implicated in its immune suppression activity.

TGF-β plays a major role in wound healing. Genetic evidence from animal models of wound healing and evidence of TGF-β antagonist-induced promotion of normal wound healing in a standard pig and rabbit skin burn/excision injury models indicate that TGF-β produced at the injury site negatively regulates wound healing by inhibiting wound re-epithelization (or epithelial cell growth). Furthermore, TGF-β induces the deposition of extracellular matrix (ECM) proteins (e.g., collagen and fibronectin) by stimulating synthesis of ECM proteins, and inhibiting degradation of these ECM proteins. Because of this potent ECM deposition-stimulating activity, TGF-β is a major factor in fibrosis including: normal wound healing and scar formation, the formation of keloid, radiation-induced fibrosis, fibromatosis, hypertrophic burn scars, and fibrosis associated with autoimmune disorders such as scleroderma and sarcoidosis.

TGF-β is also an apoptosis inducer for certain cell types, including hair follicle cells and has been implicated in regulation of the hair cycle. The hair cycle is a highly regulated process which includes three phases, anagen (growing phase), catagen (regressing phase) and telogen (resting phase). TGF-β plays an essential part of catagen of the human hair by inducing apoptosis of follicle cells, which results in the initiation of the catagen phase. Male pattern baldness is the result of premature entry into catagen phase due to excess of androgen, which up-regulates TGF-β levels. TGF-β can also act either as an inflammatory or anti-inflammatory cytokine depending on tissue types. In skin injury, TGF-β acts as a proinflammatory agent by recruiting inflammatory cells to the injury site.

In view of the wide-ranging activities of TGF-β, it is clear that over-activity of TGF-β and negative regulation in normal physiology by TGF-β have been implicated in the conditions of fibrosis, normal wound healing, inflammation, and hair growth defects. Thus, compositions that inhibit the activity of TGF-β are extremely useful in treating those conditions associated with the over-activity of TGF-β and negative regulation in normal physiology by TGF-β.

SUMMARY OF THE INVENTION

The present invention provides methods for inhibiting TGF-β actions in cells and/or tissues expressing TGF-β comprising the steps of contacting the cells and/or tissues expressing TGF-β with an amount of cholesterol or cholesterol derivative effective to inhibit the activity of TGF-β. The present invention further provides a method for treating a condition associated with overactivity of TGF-β or negative regulation (in normal physiology) by TGF-β in a subject in need of treatment, comprising contacting cells and/or tissue expressing or overexpressing TGF-β in the subject with an amount of cholesterol or cholesterol derivatives effective to inhibit activity of TGF-β, thereby treating and/or preventing conditions such as skin fibrosis, dermal wounds, inflammations and baldness, collective referred to herein as "dermal conditions". In a preferred embodiment, the cholesterol derivative is oxidized 7-DHC.

Cells were treated with increasing concentrations of cholesterol, as indicated (A, B, C), 50 µg protein/ml LDL (D), 5 µg protein/ml VLDL (D) or 50 µg/ml cholesterol (E) at 37° C. for 1 hr and then further incubated with 50 pM TGF-$β_1$ for 30 min. Phosphorylated Smad2 (P-Smad2) and total Smad2 in the cell lysates were analyzed by 7.5% SDS-PAGE and followed by immunoblot analysis using anti-P-Smad2 and anti-Smad2 antibodies. A representative of a total of 3 analyses is shown (top). The quantitative analysis of the immunoblots is shown (bottom). The data bar represents the mean±S.D. *,** significantly lower than that in cells treated with TGF-$β_1$ only $p<0.001$ and $p<0.05$, respectively. Smad2 nuclear translocation was analyzed by indirect immunofluorescent staining using P-Smad2 antibody and rhodamine-labeled 2nd antibody (E). Rhodamine fluorescence represents P-Smad2 staining (a,b,c) whereas the nuclei were stained by DAPI staining (d,e,f). The arrow indicates cells which did not exhibit nuclear localization of Smad2 (c).

Figure 2:
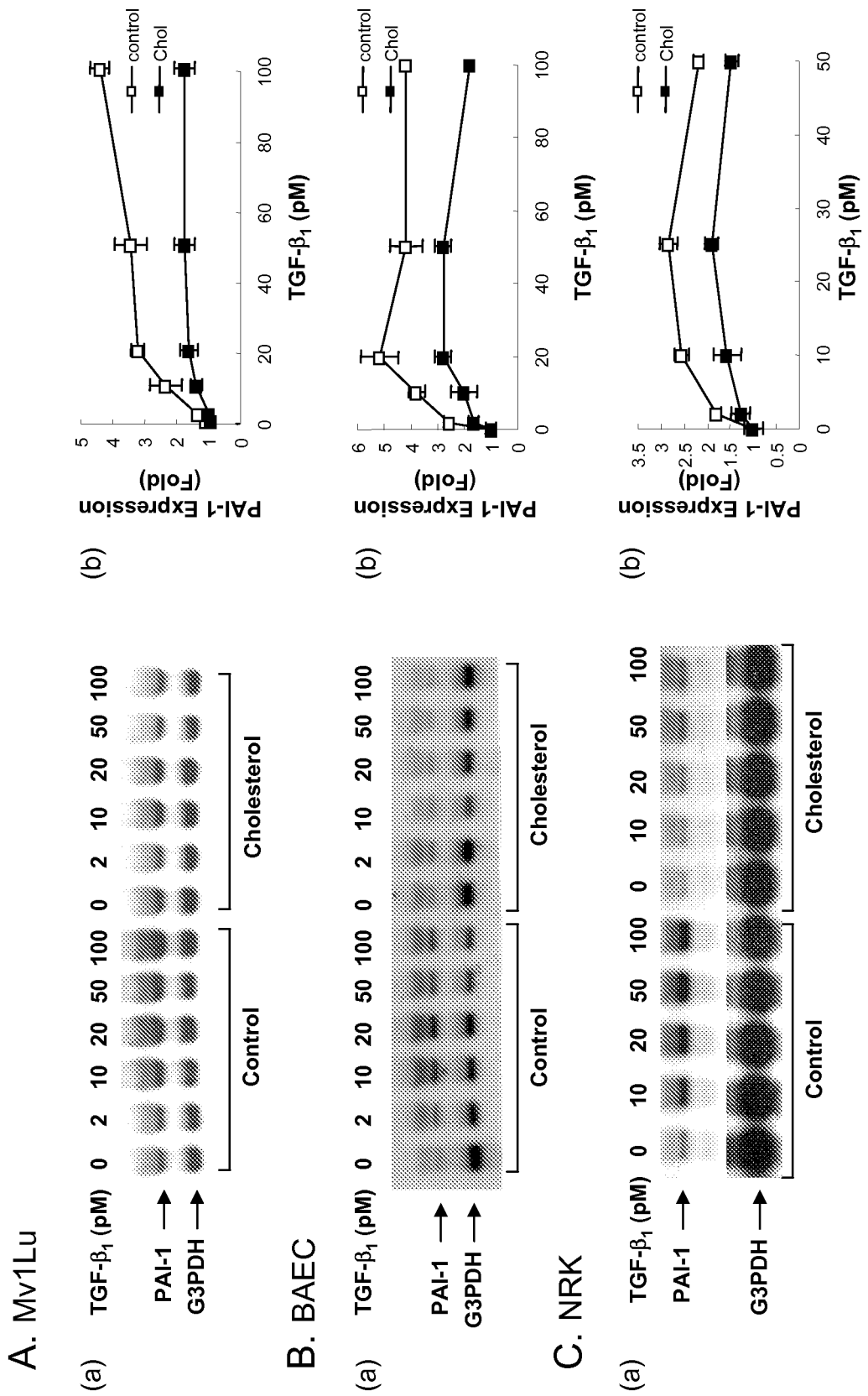
Figure 2:
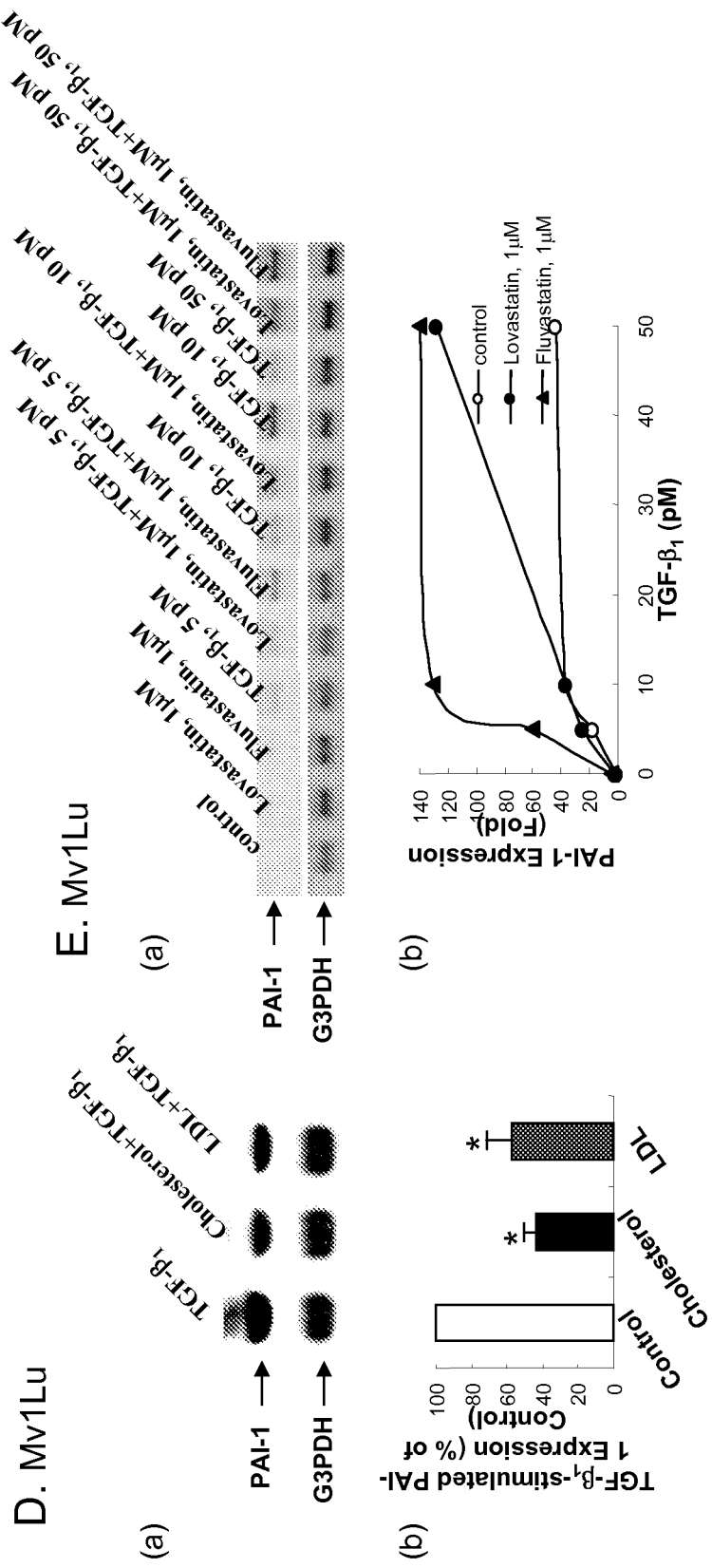
Figure 2:
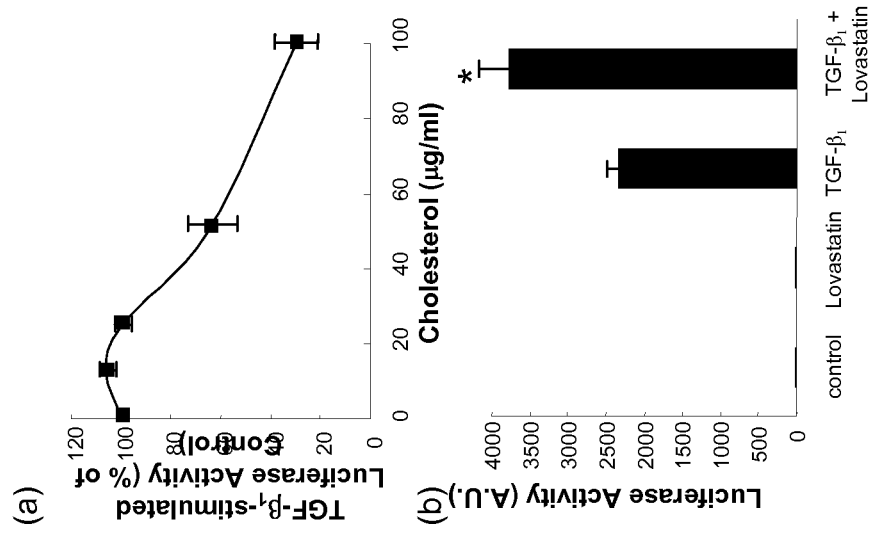
Figure 2:
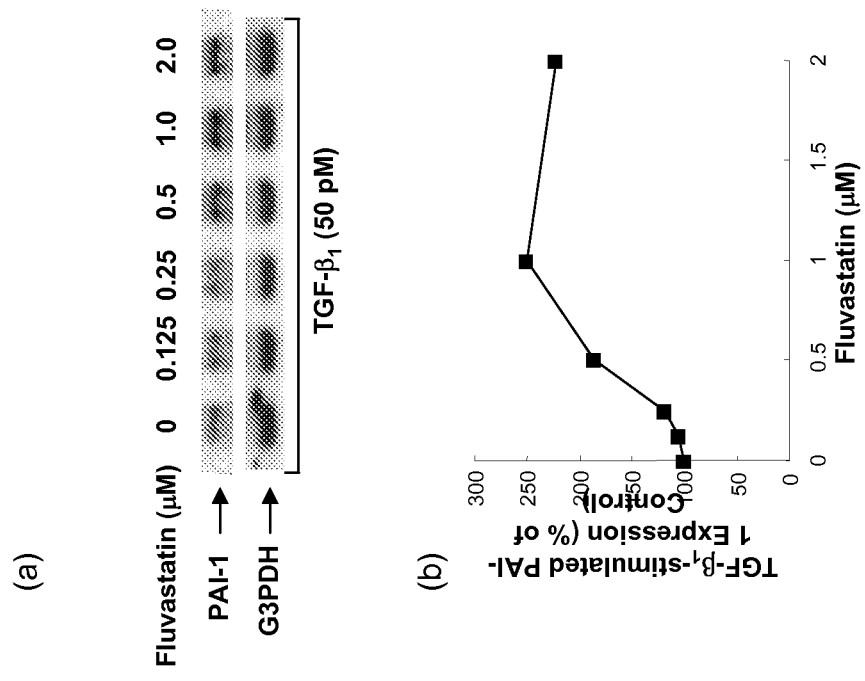
Figure 2:
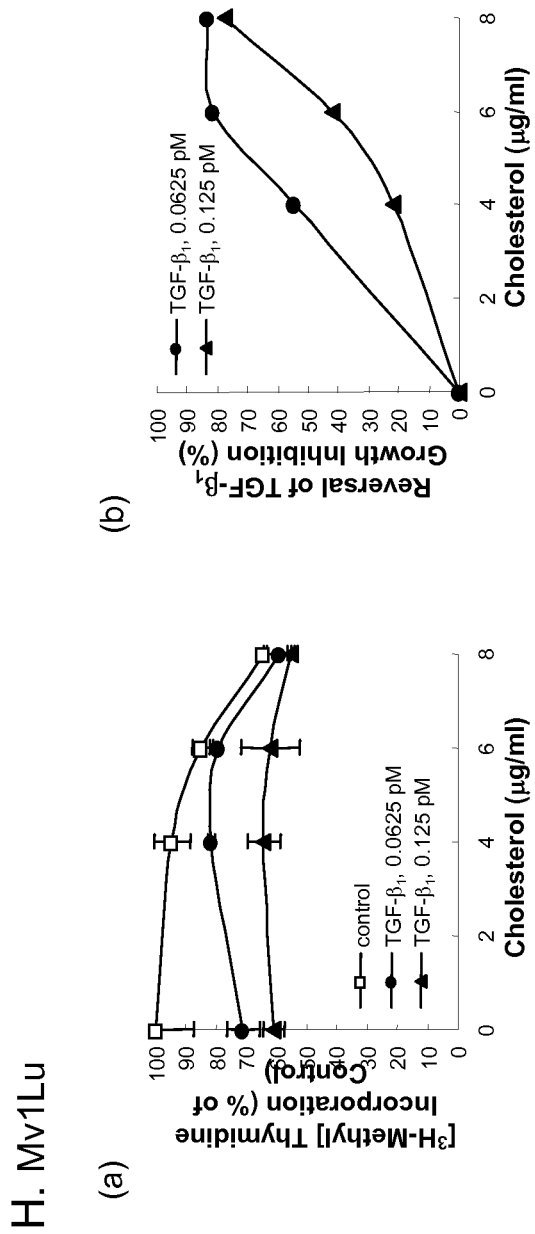

FIG. 2: Effect of cholesterol, LDL and statins on TGF-$β_1$-induced PAI-1 expression (A, B, C, D, E, F), luciferase reporter gene expression (G) and growth inhibition (H) in Mv1Lu, BAEC and NRK cells.

(A, B, C, D, E, F) Cells were treated with 50 µg/ml cholesterol (A, B, C, D) and 50 µg/ml LDL (D) at 37° C. for 1 hr or with 1 µM fluvastatin or lovastatin (E) or several concentrations of fluvastatin (F) at 37° C. for 16 hr and then further incubated with increasing concentrations (as indicated) of TGF-$β_1$ (A, B, C, E) or 50 pM TGF-$β_1$ (D,F) for 2 hr. Northern blot analysis of PAI-1 and G3PDH was performed. A representative of a total of three analyses is shown (a). The relative intensities of the transcripts were quantified with a Phospho-Imager. The ratio of the relative intensities of PAI-1 and G3PDH transcripts in cells treated without TGF-$β_1$ and cholesterol, LDL or statins on the blot was taken as 1 fold or 100% of PAI-1 expression. The quantitative data from three independent analyses is shown (b). The data bar represents the mean±S.D. * significantly lower than that in cells treated with the same concentration of TGF-$β_1$ but without cholesterol (A, B, C) or with TGF-$β_1$ only (D): $p<0.001$. (G) Mv1Lu cells stably expressing a luciferase reporter gene driven by the PAI-1 promoter (MLECs-clone 32) were treated with increasing concentrations (as indicated) of cholesterol at 37 EC for 1 hr (a) or with 1 μM lovastatin at 37° C. for 16 hr (b) and then further incubated with 50 pM TGF-β for 7 hr. The luciferase activity in cells treated without cholesterol was taken as 100% (a). The luciferase activity of the cell lysates was determined and expressed as arbitrary units (A.U.) (b). * significantly lower or higher than that in cells treated with TGF-$β_1$ alone: p<0.001. (H) Cells were incubated with 0.0625 and 0.125 pM TGF-$β_1$ in the presence of increasing concentrations of cholesterol, as indicated. After 18 hr at 37° C., cell growth was determined by measurement of [$^3$H-methyl]thymidine incorporation into cellular DNA (a). The [$^3$H-methyl]thymidine incorporation in cells treated with vehicle only (T1); with TGF-$β_1$ (T2); with cholesterol (T3); with cholesterol and TGF-$β_1$ (T4) was measured. T1 was taken as 100%. The degree (%) of cholesterol-mediated reversal of TGF-$β_1$ growth inhibition was estimated by the equation:

$$\% \text{ reversal} = [1-(T3-T4/T1-T2)] \times 100$$

Cholesterol appeared to reverse TGF-$β_1$ growth inhibition in a dose-dependent manner (b). The experiments were carried out in triplicate.

Figure 3:
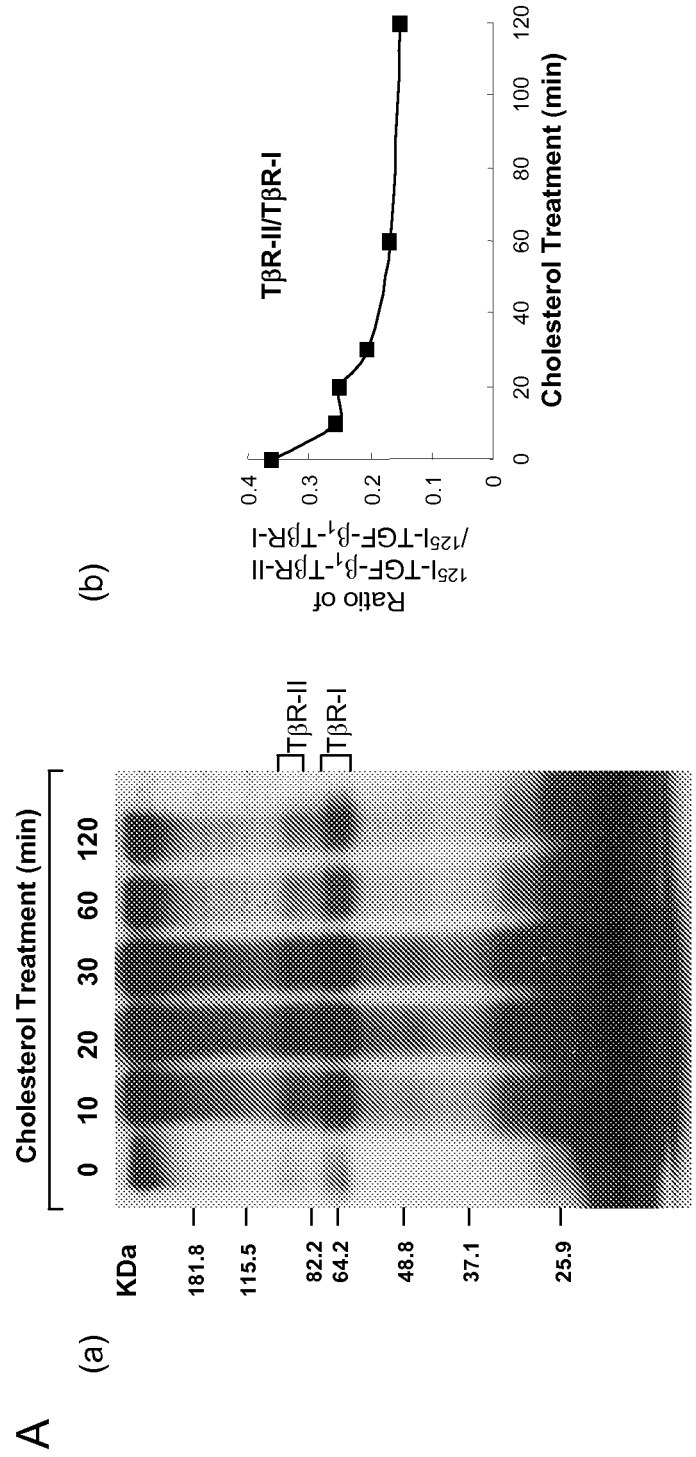
Figure 3:
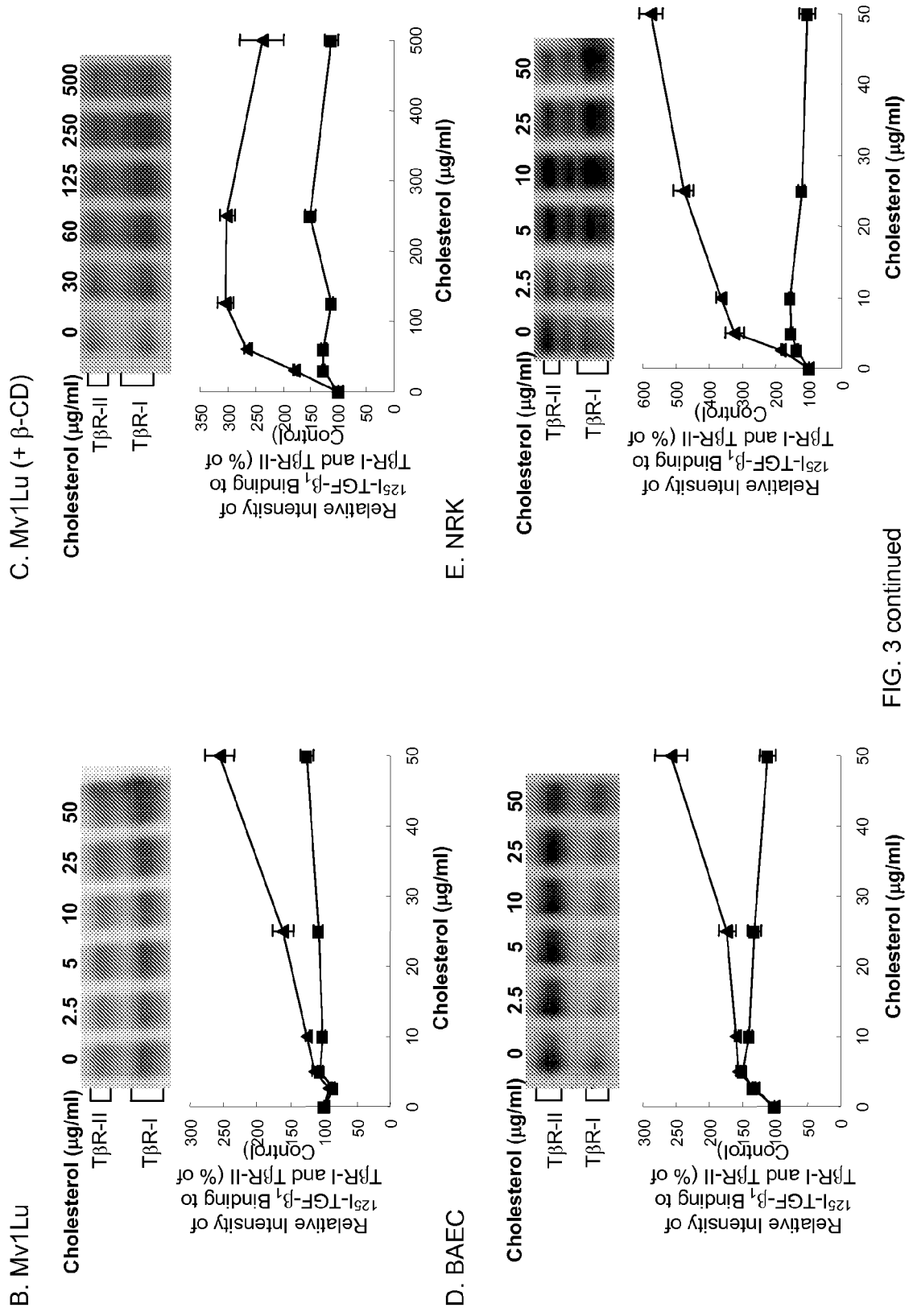
Figure 3:
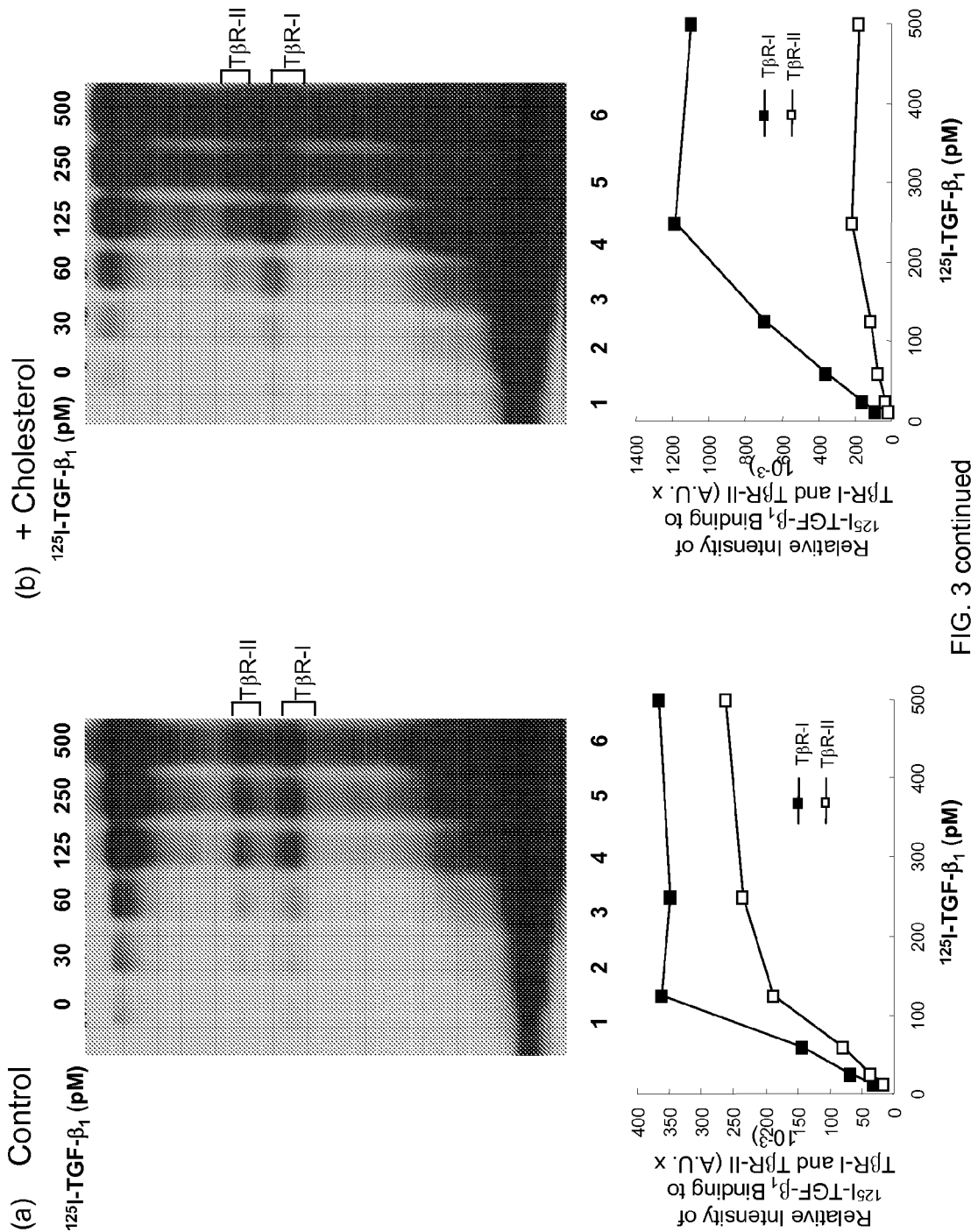

FIG. 3: Effect of cholesterol on $^{125}$I-TGF-$β_1$ binding to TβR-I and TβR-II in a time (A) and concentration (B, C, D, E)-dependent but TGF-β receptor affinity (F)-independent manner in Mv1Lu, BAEC and NRK cells.

(A) Mv1Lu cells were treated with 50 μg/ml cholesterol at 37° C. After several time periods, as indicated, $^{125}$I-TGF-$β_1$-affinity labeling was performed at 0° C. $^{125}$I-TGF-$β_1$ affinity-labeled TGF-β receptors were analyzed by 7.5% SDS-PAGE and autoradiography (a) and quantified with a PhosphoImager. The bracket indicates the locations of $^{125}$I-TGF-$β_1$ affinity-labeled TβR-I and TβR-II. The ratio of $^{125}$I-TGF-$β_1$ binding to TβR-II and TβR-I is plotted against incubation time (b).

(B, C, D, E) Cells were treated with increasing concentrations of cholesterol in the presence (C) and absence (B, D, E) of 0.2% β-CD, as indicated. After 1 hr at 37° C., $^{125}$I-TGF-$β_1$ affinity labeling of TβR-I and TβR-II in cells was performed at 0° C. $^{125}$I-TGF-$β_1$ affinity-labeled TβR-I and TβR-II were analyzed by 7.5% SDS-PAGE and autoradiography or quantified with a PhosphoImager. A representative of a total of three analyses is shown (top). The bracket indicates the locations of $^{125}$I-TGF-β affinity-labeled TβR-I and TβR-II. The relative intensities of $^{125}$I-TGF-$β_1$ affinity-labeled TβR-I and TβR-II in cells treated without cholesterol were taken as 100%. The quantitative data from three analyses is shown (bottom). The data bar represents the mean±S.D. * significantly higher than that in cells treated with TGF-$β_1$ alone: p<0.001.

(F) Cells were treated with (b) or without (a) 50 μg/ml cholesterol at 37° C. for 1 hr. $^{125}$I-TGF-$β_1$ affinity labeling was performed after incubating cells with increasing concentrations of $^{125}$I-TGF-$β_1$ as indicated at 0° C. for 2.5 hr. $^{125}$I-TGF-$β_1$ affinity-labeled TβR-I and TβR-II were analyzed by 7.5% SDS-PAGE and autoradiography (top). The bracket indicates the locations of $^{125}$I-TGF-$β_1$ affinity-labeled TβR-I and TβR-II. The relative intensities of $^{125}$I-TGF-$β_1$-TβR-I and $^{125}$I-TGF-$β_1$-TβR-II complexes, which were quantified with a PhosphoImager, are plotted against TGF-$β_1$ concentrations (bottom).

Figure 4:
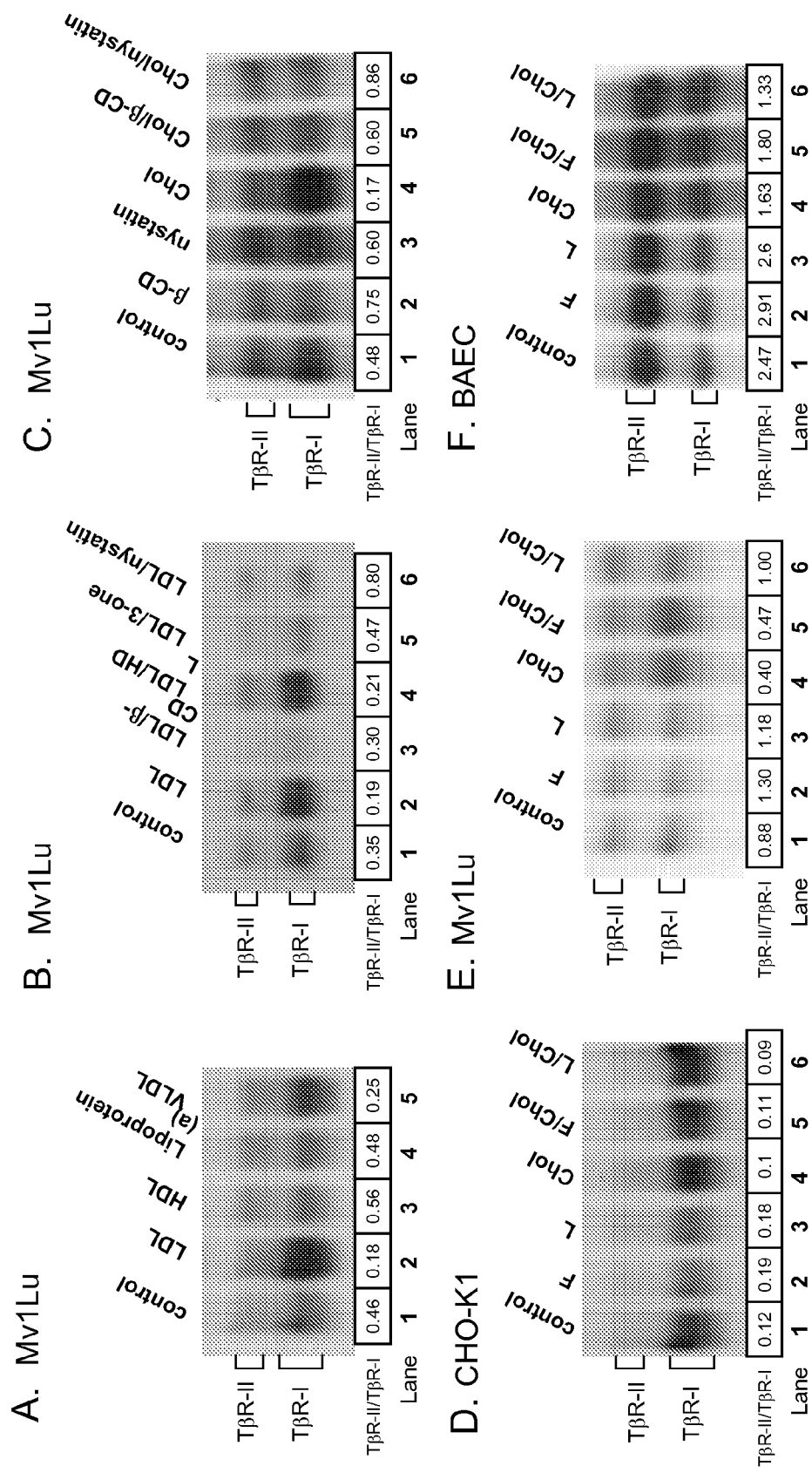
Figure 4:
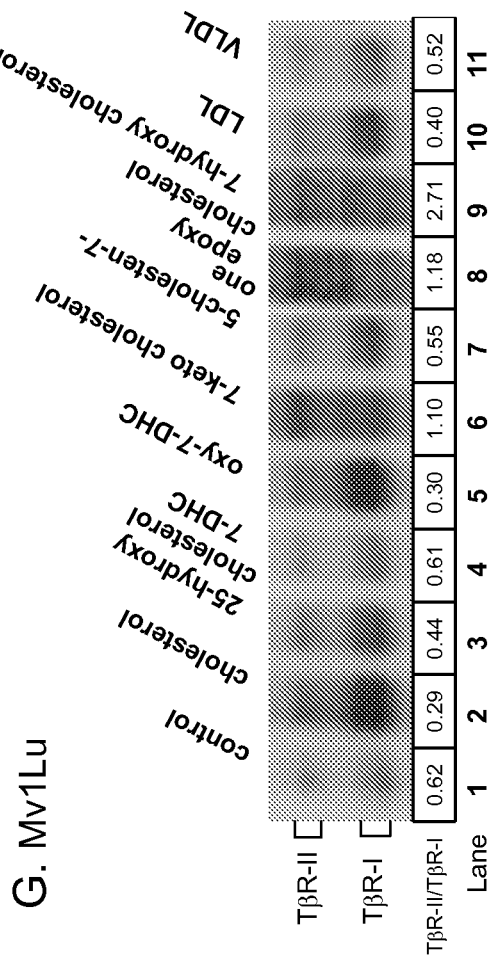

FIG. 4: Effects of LDL/VLDL/HDL, fluvastatin/lovastatin and nystatin/β-CD (A, B, C, D, E, F) and of cholesterol analogs and derivatives (G) on $^{125}$I-TGF-$β_1$ binding to TβR-I and TβR-II in Mv1Lu, BAEC and CHO-K1 cells.

(A, B, C, D, E, F) Cells were treated with LDL (50 μg protein/ml), VLDL (5 μg protein/ml), HDL (50 μg protein/ml), lipoprotein (a) (10 μg/ml), fluvastatin (F; 1 μM), lovastatin (L; 1 μM), nystatin (Nys; 25 μg/ml), β-CD (β-CD; 8 mM), cholest-4-en-3-one (3-one; 50 μg/ml) or cholesterol (Chol; 50 μg/ml) alone or combination of two. After 1 hr at 37° C. or 16 hr at 37° C. (for fluvastatin and lovastatin), $^{125}$I-TGF-$β_1$ affinity labeling of cell-surface TGF-β receptors was performed at 0° C. $^{125}$I-TGF-$β_1$ affinity-labeled TβR-I and TβR-II were analyzed by 7.5% SDS-PAGE and autoradiography. The relative intensities of TβR-I and TβR-II were quantified with a PhosphoImager. The ratio of $^{125}$I-TGF-$β_1$ binding to TβR-II and TβR-I were estimated. The numbers above the lane sequence denote the ratio of TβR-II/TβR-I.

(G) Mv1Lu cells were treated with 50 μg/ml of cholesterol and cholesterol analogs/derivatives including 25-hydroxycholesterol, 7-dehydrocholesterol (7-DHC), 7-ketocholesterol, 7β, 8β-epoxycholesterol, 7β-hydroxycholesterol, and oxidized 7-dehydrocholesterol (oxy-7DHC). After 1 hr at 37° C., $^{125}$I-TGF-$β_1$ affinity labeling of TGF-β receptors was performed. $^{125}$I-TGF-$β_1$ affinity-labeled TβR-I and TβR-II were analyzed by 7.5% SDS-PAGE and autoradiography. The bracket indicates the locations of $^{125}$I-TGF-$β_1$-affinity-labeled TβR-I and TβR-II. The relative intensities of $^{125}$I-TGF-$β_1$ affinity-labeled TβR-I and TβR-II were determined by a PhosphoImager. The ratios of $^{125}$I-TGF-$β_1$ binding to TβR-II and TβR-I were estimated. The numbers above the lane sequence denote the ratio of TβR-II/TβR-I.

Figure 5:
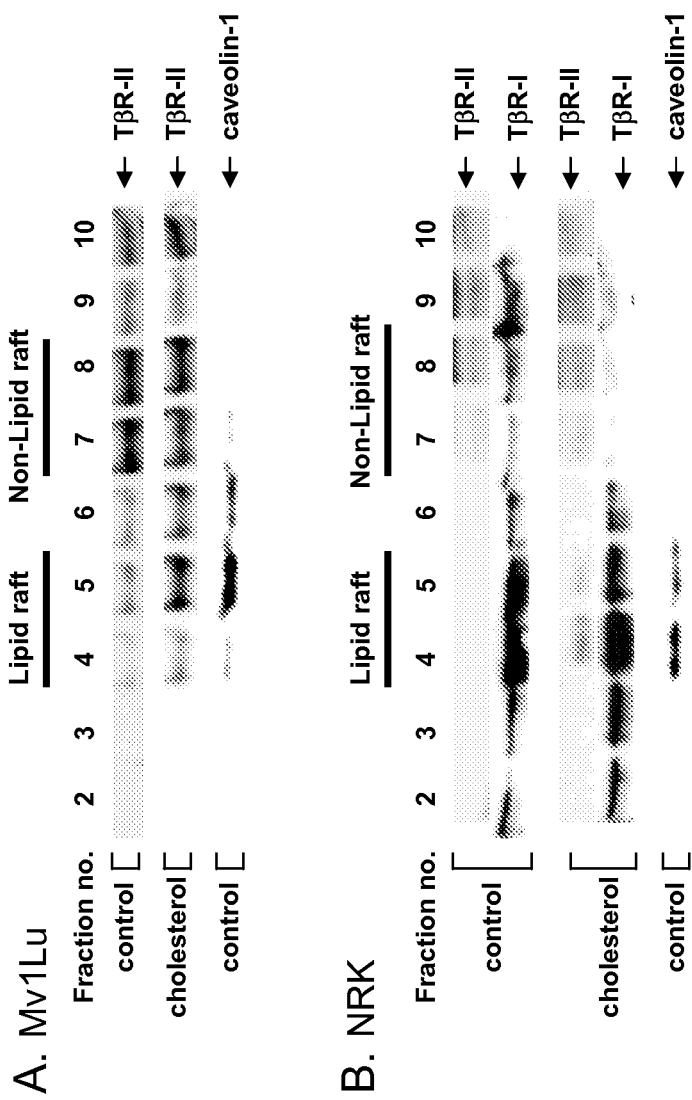
Figure 5:
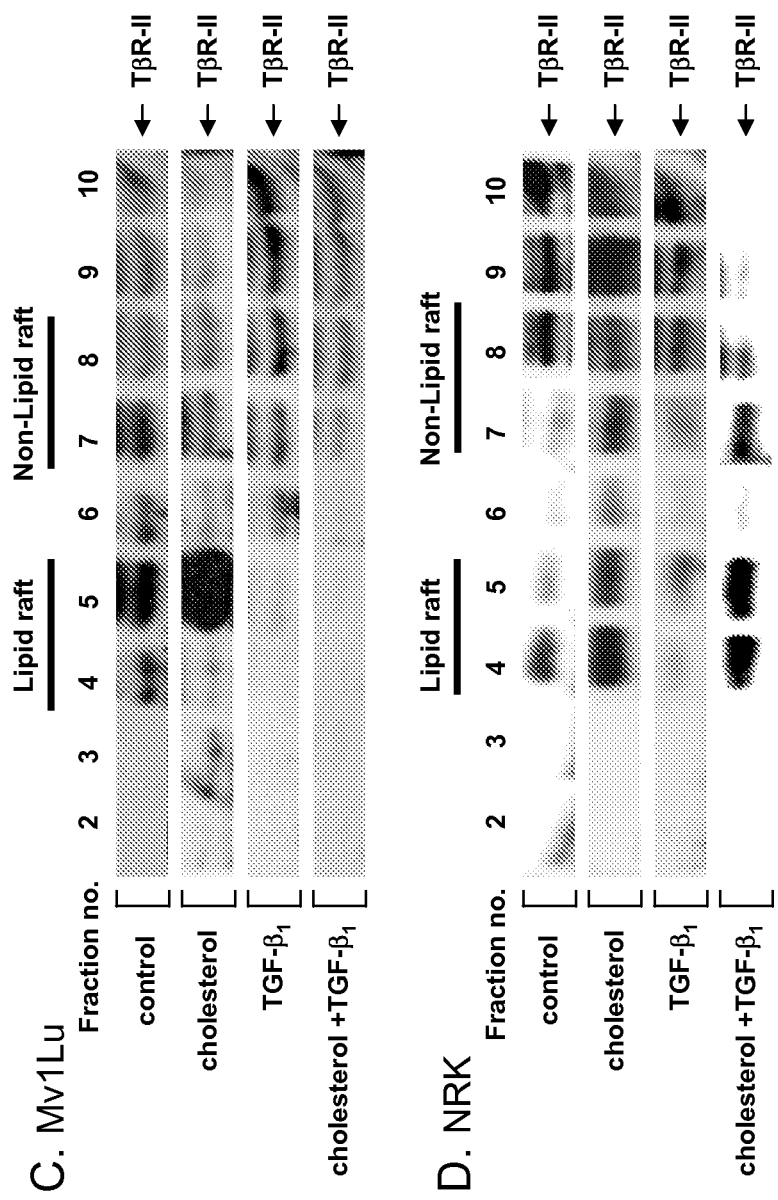
Figure 5:
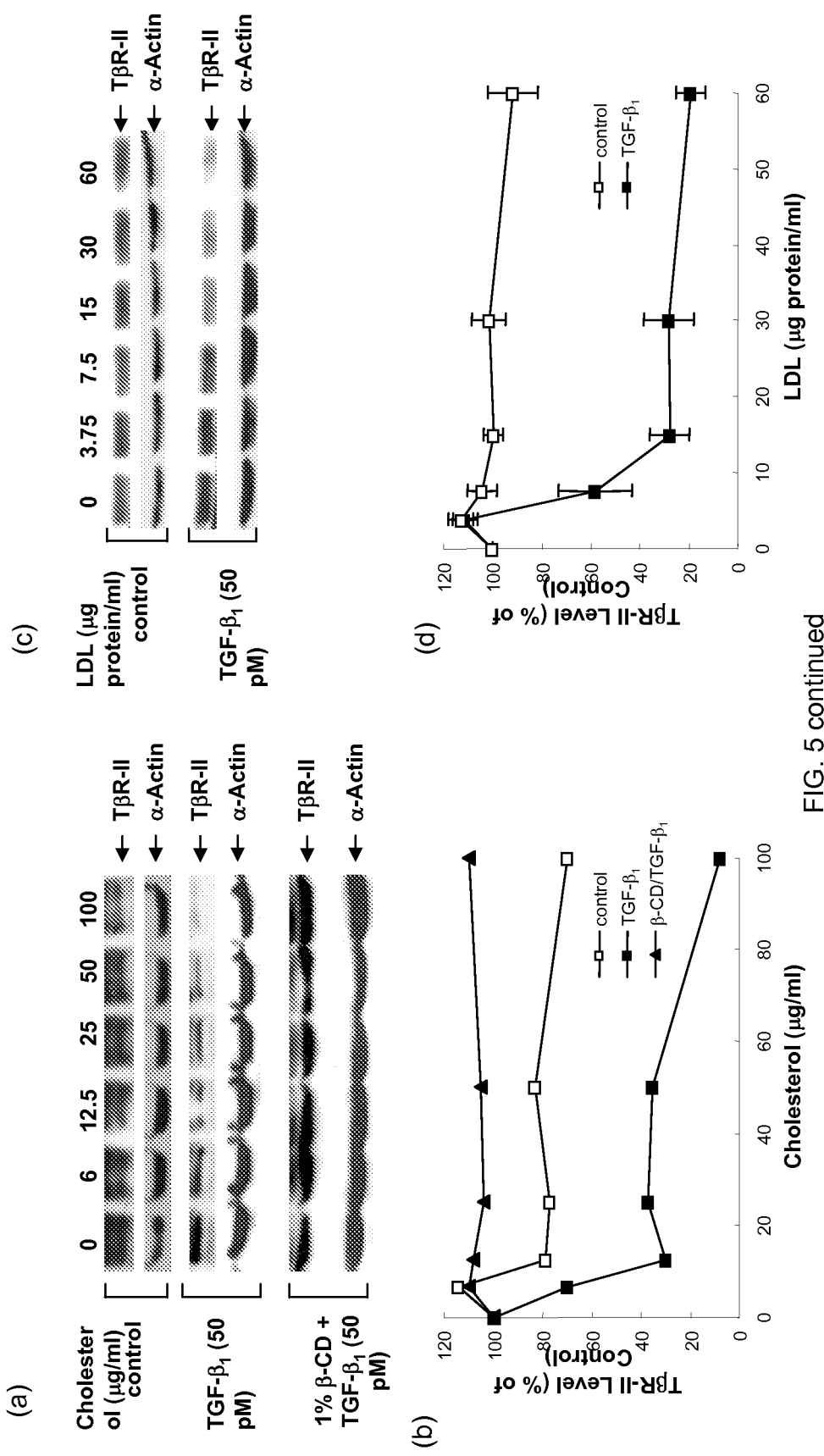
Figure 5:
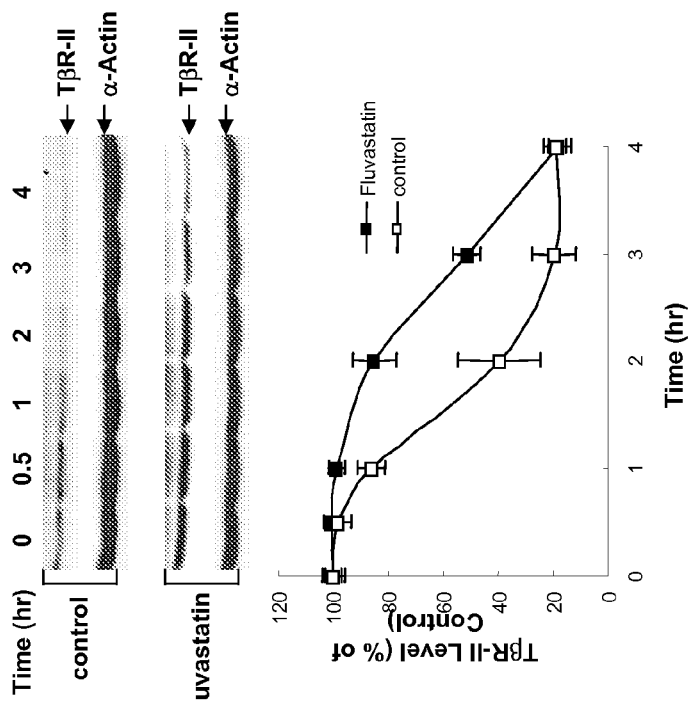
Figure 5:
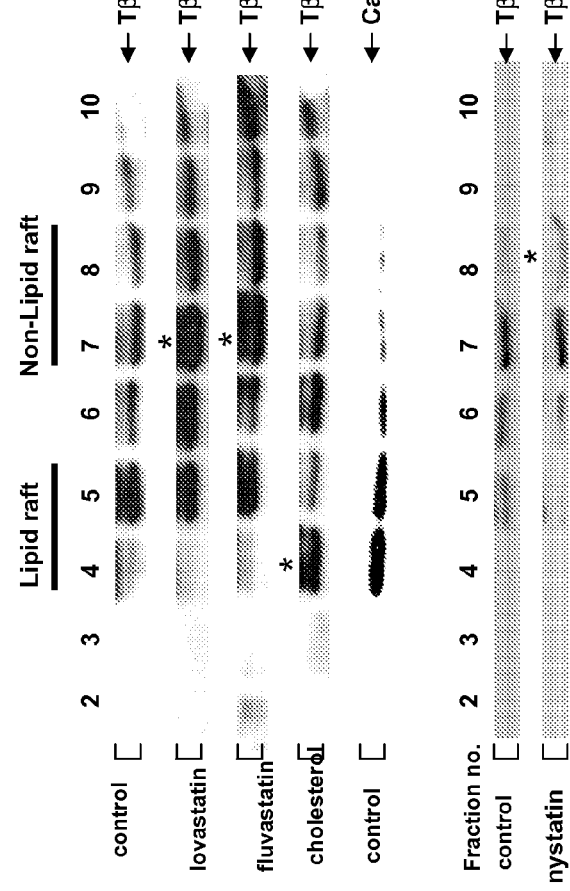

FIG. 5: Effect of cholesterol (A,B,C,D,E), LDL (E) or cholesterol-lowering agents (F,G) on the plasma-membrane microdomain localization (A,B,C,D,F) and TGF-$β_1$-induced degradation (C,D,E,G) of TβR-I and TβR-II in Mv1Lu and NRK cells.

(A, B, C, D) Cells were treated with or without 50 μg/ml cholesterol (A,B,C,D) or several concentrations of cholesterol, as indicated in the presence and absence of 1% β-CD (E) at 37° C. for 1 hr and further incubated with (C,D) and without (A,B) 50 pM TGF-$β_1$ for 1 hr. The cell lysates from these treated cells were subjected to sucrose density gradient ultracentrifugation. After ultracentrifugation, fractions were collected and analyzed by 7.5% SDS-PAGE followed by Western blot analysis using antibodies to TβR-I, TβR-II and caveolin-1. The TβR-I in Mv1Lu cells was not analyzed due to the fact that anti-TβR-I antibody used in the experiments did not react well with mink TβR-I. The arrow indicates the locations of TβR-I, TβR-II and caveolin-1. Fractions 4 and 5 represent fractions containing lipid rafts/caveolae whereas fractions 7 and 8 represent non-lipid raft fractions.

(E) Cells were treated with several concentrations of cholesterol (a,b) or LDL (c,d) as indicated in the presence and absence of 1% β-CD at 37° C. for 1 hr and further incubated with 50 pM TGF-β for 1 hr. The cell lysates were then subjected to 7.5% SDS-PAGE and Western blot analysis using antibodies to TβR-II and α-actin (a,c). The relative intensities of TβR-II and α-actin on the blot were quantified by densitometry (b,d). The ratio of the relative intensities of TβR-II and α-actin in cells treated without TGF-$β_1$ was taken as the 100% level of TβR-II. The data is representative of a total of three independent analyses. *Significantly lower than control cells: p<0.001.

(F, G) Cells were treated with or without 1 μM lovastatin/fluvastatin or nystatin (25 μg/ml)/cholesterol (50 μg/ml) at 37° C. for 16 hr or 1 hr, respectively. The treated cells were directly analyzed by sucrose density gradient ultracentrifugation analysis (F) or further incubated with 50 pM TGF-β at 37° C. for several time periods as indicated (G). Western blot analysis of the sucrose density gradient fractions (F) and of TGF-$\beta_1$-treated cell lysates (G) was performed using antibody to T$\beta$R-II. The relative levels of T$\beta$R-II and $\alpha$-actin were quantified by densitometry. Fractions 4/5 and 7 represent lipid raft/caveolae and non-lipid raft fractions, respectively. The asterisk (*) indicates the increased level of T$\beta$R-II in the fraction (F). The ratio of the relative intensities of T$\beta$R-II and $\alpha$-actin in cells treated without TGF-$\beta_1$ was taken as 100% of the T$\beta$R-II level. A representative of a total of three independent analyses is shown (G, top). The quantitative data from three independent analyses is shown (G, bottom). The data bar represents the mean±S.D.

Figure 6:
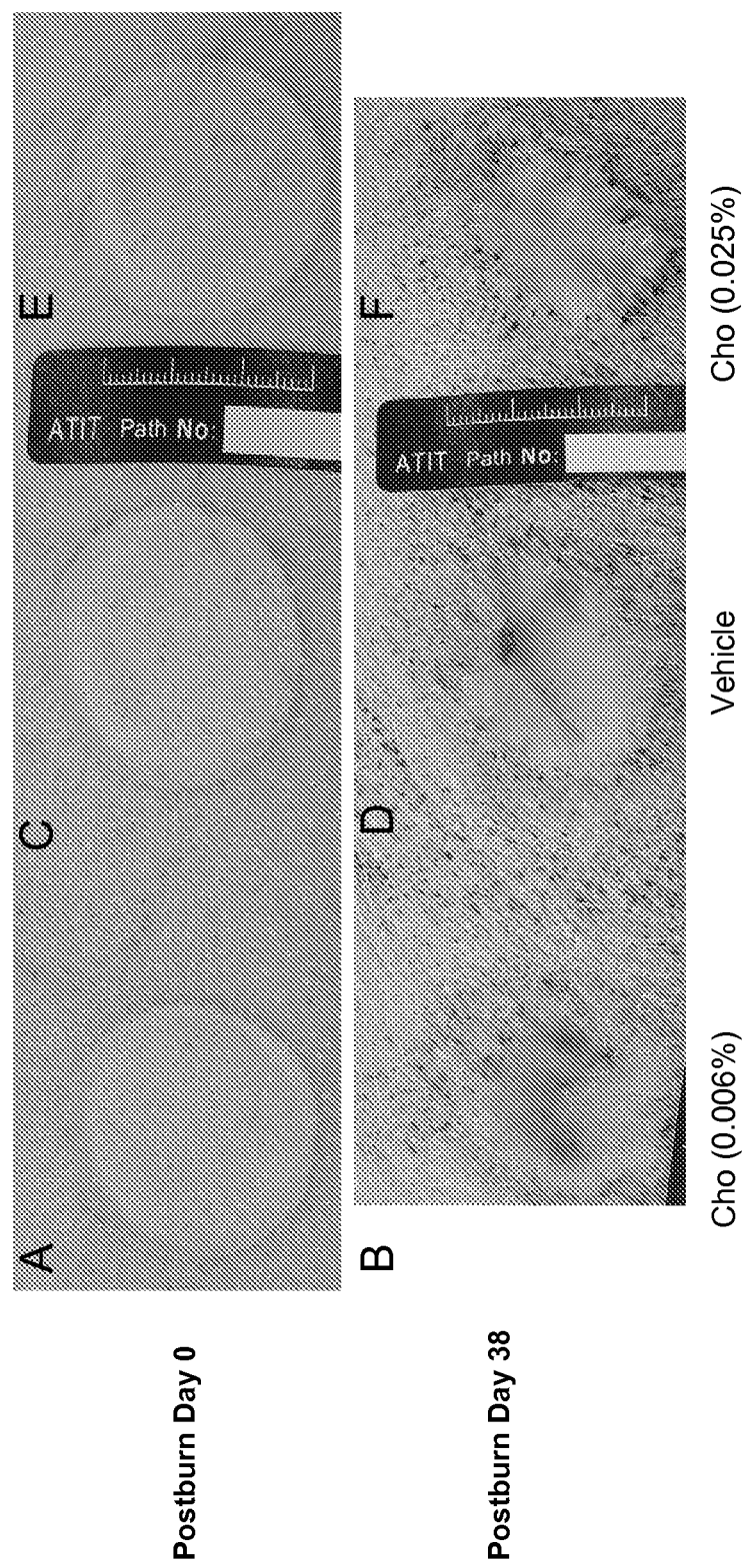

FIG. 6. Wound closure and scar formation in pig burn wounds treated with cholesterol (CHO). Burn wounds treated with 0.025% cholesterol (A,B) and 0.00625% cholesterol (E,F) and vehicle only (C,D) were photographed immediately after burn injury (A,C,E) and at postburn day 38 (B,D,F). After burn injury, necrosis was present (white) (A,C,E). The control wound exhibited an area of open wound (D). In contrast, the wound treated with 0.00625% and 0.025% cholesterol showed no (F) or very little open wound (B). Less scar formation was seen in the wounds treated with cholesterol (B,F) than the control wound (D).

Figure 7:
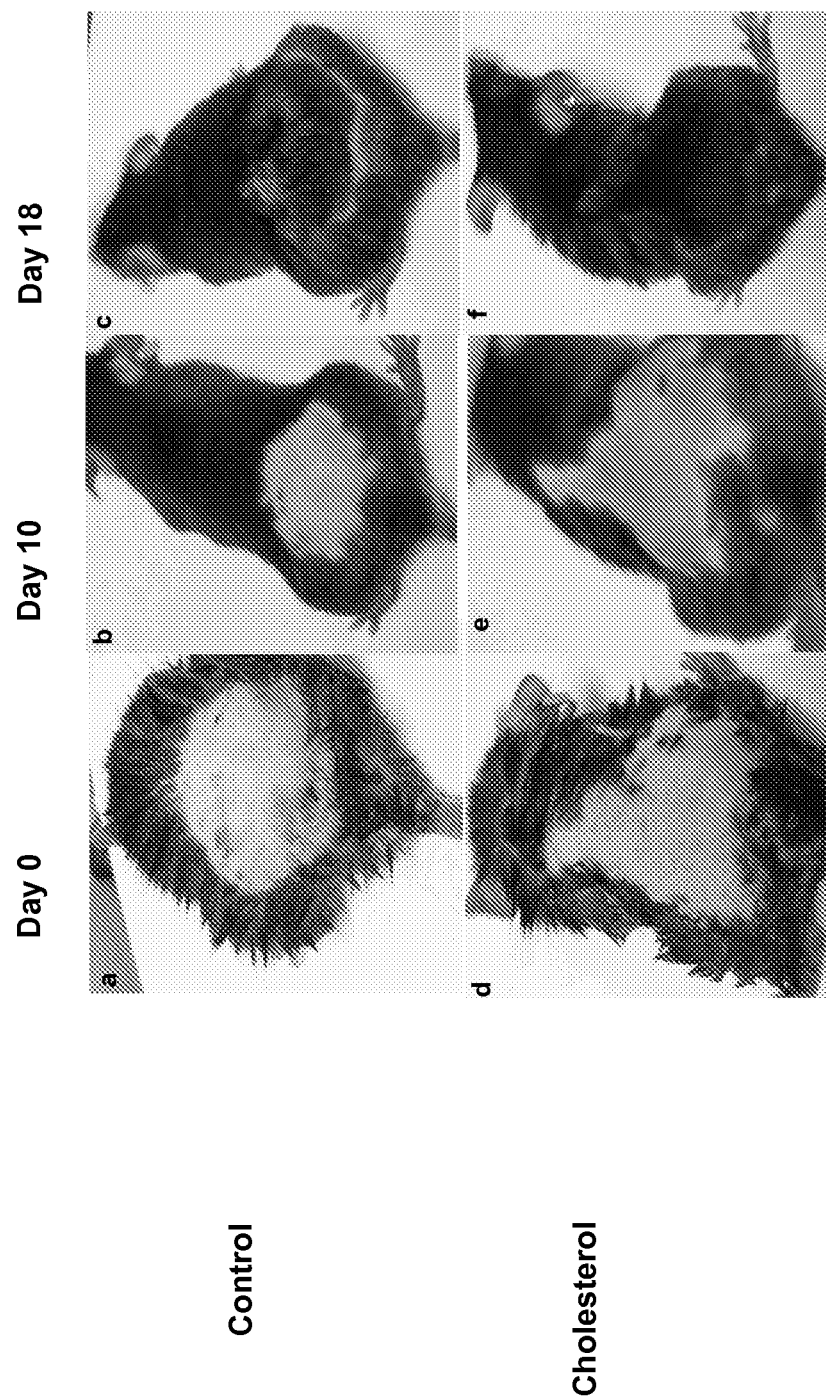

FIG. 7. Hair growth promotion in mice topically treated with cholesterol. Mice (female, 6 weeks old) were subjected to hair removal by using hair remover lotion Nair®. The areas after hair removal were treated with the lotion containing vehicle only or 0.025% cholesterol on the first day and every other two days. Photographs were taken immediately after hair removal and prior to topical application with vehicle (a,b,c) or lotion containing cholesterol (d,e,f). Photographs were taken at days 0 (a,d), 10 (b,e) and 18 (c,f). The dark color indicates an early stage of hair growth.

DETAILED DESCRIPTION OF THE INVENTION

The present invention is based upon the discovery that cholesterol or cholesterol derivatives inhibit the activity of TGF-$\beta$. On the basis of this finding, the present invention provides a method for inhibiting activity of TGF-$\beta$, comprising contacting tissue expressing TGF-$\beta$, with cholesterol or its derivatives (oxy-7-DHC).

The methods of the present invention may be used to inhibit activity of TGF-$\beta$ in vitro or in vivo. As used herein, the term "inhibit activity of TGF-$\beta$." means inhibit the signaling mechanisms of TGF-$\beta$, as disclosed herein, including Smad2 phosphorylation, Smad2/3 heterooligomerization, and nuclear translocation, as well as associated downstream transcriptions. Inhibition of these signaling mechanisms by TGF-$\beta$ may be detected by known procedures, including any of the methods, molecular procedures, and assays disclosed herein.

As used herein the "subject" is preferably a mammal (e.g., humans, domestic animals, and commercial animals), and is most preferably a human. When tissue expressing TGF-$\beta$ is localized to a particular portion of the body of the subject, it may be desirable to introduce cholesterol or cholesterol derivatives directly to the skin tissue by topical, intradermal and transdermal administration. The amount of cholesterol or cholesterol derivatives to be used is an amount effective to inhibit activity of TGF-$\beta$, and may be readily determined by the skilled artisan.

The ability of cholesterol or cholesterol derivative to inhibit activity of TGF-$\beta$ is particularly useful for treating conditions associated with overactivity of TGF-$\beta$ and negative regulation (in normal physiology) by TGF-$\beta$. As used herein, "overactivity of TGF-$\beta$" includes pathologic activity of TGF-$\beta$ and pathologic expression of TGF-$\beta$ in a particular tissue, as compared with normal activity of TGF-$\beta$ and normal expression of TGF-$\beta$ in the same type of tissue. "Negative regulation in normal physiology by TGF-$\beta$" includes the inhibitory role of TGF-$\beta$ in wound re-epithelialization of normal wound healing and TGF-$\beta$-mediated regression of hair follicles in hair cycle of normal hair growth. It is believed that, by inhibiting activity of TGF-$\beta$, cholesterol and cholesterol derivatives will be useful for the treatment of conditions associated with the overactivity and negative regulation in normal physiology by TGF-$\beta$. It is further believed that cholesterol and cholesterol derivatives would be effective either alone or in combination with therapeutic agents, such as antibiotics which are typically used in the treatment of these conditions.

Accordingly, the present invention provides a method for treating a condition associated with overactivity of TGF-$\beta$ or negative regulation in normal physiology by TGF-$\beta$. TGF-$\beta$ in a subject in need of treatment, comprising contacting tissue expressing TGF-$\beta$ in the subject with an amount of cholesterol or cholesterol derivative effective to inhibit activity of TGF-$\beta$, thereby treating and/or preventing the conditions. "Negative regulation in normal physiology by TGF-$\beta$" includes normal wound healing processes and the hair follicle growth cycle. TGF-$\beta$ negatively regulates the process of normal wound healing. It also mediates hair follicle regression (catagen).

Overactivity of TGF-$\beta$ and negative regulation in normal physiology by TGF-$\beta$ may be associated with such conditions as skin fibrosis, wound healing defects, baldness and inflammation. In the method of the present invention, cholesterol or cholesterol derivatives may be used to treat forms of skin fibrosis, including, without limitation, the following: scars, particularly scars caused by burning, radiation or chemicals, keloid; autoimmune disorders leading to fibrosis, particularly scleroderma; post-surgical fibrosis, particularly fibrosis induced by surgery or surgical manipulation In accordance with the method of the present invention, cholesterol and cholesterol analogues may further be used to enhance normal wound healing and to attenuate inflammation and androgen-dependent and -independent baldness.

In one preferred embodiment, the present invention provides a method for treating a subject having fibrosis, comprising administering to the subject an amount of cholesterol or cholesterol derivative effective to treat a skin wound and fibrosis. As used herein, the phrase "effective to treat skin wounds and fibrosis" means effective to promote wound healing and ameliorate or minimize the clinical impairment or symptoms of the skin fibrosis. For example, where the fibrosis is keloids, the amount of cholesterol or cholesterol derivative effective to treat the fibrosis is that which can ameliorate or minimize the process of fibrosis. The amount of cholesterol or cholesterol derivatives effective to treat fibrosis in a subject in need of treatment will vary depending upon the particular factors of each case, including the type of fibrosis. This amount can be readily determined by the skilled artisan.

According to the method of the present invention, cholesterol or cholesterol derivatives may be administered to a human or animal subject by known procedures, including, without limitation, topical, intracutaneous injection and transdermal administration. In a preferred embodiment, the cholesterol or cholesterol derivatives may be applied topically. Cholesterol or cholesterol derivative can be applied in any type of cosmetically or pharmaceutically acceptable vehicle for topical application with which the active component is compatible, e.g., a gel, a cream, a lotion, an ointment, a mousse, a spray, a solid stick, a powder, a suspension, a dispersion, and the like. Preferably, however, the cholesterol or cholesterol derivatives are formulated in a composition containing emulsifiers. Techniques for formulation of various types of vehicles are well known to those skilled in the art, and can be found, for example, in Chemistry and Technology of the Cosmetics and Toiletries Industry, Williams and Schmitt, eds., Blackie Academic and Professional, Second Edition, 1996, and Remington's Pharmaceutical Sciences, 18th Edition, 1990, the contents of which are incorporated herein by reference.

For transdermal administration, cholesterol or cholesterol derivative may be combined with skin penetration enhancers, such as propylene glycol, polyethylene glycol, isopropanol, ethanol, oleic acid, N-methylpyrrolidone, and the like, which increase the permeability of the skin to the cholesterol and cholesterol derivatives permit the cholesterol or cholesterol derivatives to penetrate through the skin. The compositions comprising cholesterol or cholesterol derivative in combination with enhancer also may be further combined with a polymeric substance, such as ethylcellulose, hydroxypropyl cellulose, ethylene/vinylacetate, polyvinyl pyrrolidone, and the like, to provide the composition in lotion or cream form, which may be dissolved in solvent such as methylene chloride, evaporated to the desired viscosity, and then applied to backing material to provide a patch.

It is preferred that cholesterol or cholesterol derivatives be combined with other components of the naturally occurring lipid barrier. In a particularly preferred embodiment, the cholesterol or cholesterol derivatives are combined with ceramides, and a sterol, preferably cholesterol. Preferred ceramides include sphingolipids, having a sphingosine or related molecule backbone with fatty acids or ω-esterified fatty acids linked to an amino group on the sphingosine, and in some cases, with saccharide moieties linked to the terminal hydroxyl of the sphingosine. In particular, the compositions may contain ω-esterified ceramides or acylceramides, cerebrosides, ω-esterified cerebrosides, or acylglycosyl sphingolipids. Particularly preferred types of ceramides for the present compositions are ceramide III and cerebrosides.

In those compositions in which cholesterol or cholesterol derivatives are combined with these lipids, the cholesterol can be used in an amount of from about 0.005 to 1%, preferably 0.01 to about 0.5%, most preferably about 0.02 to about 0.2%, all by weight of the total composition. In a particularly preferred embodiment, the cholesterol or cholesterol derivative and the lipid components are present in substantially equal amounts in the composition. It will be understood from the foregoing that the lipid component need not be pure lipid, but rather may be natural extracts containing one or more desirable lipids, and used in amounts consistent with attaining the concentrations recommended above.

The invention is further illustrated by the following non limiting examples.

EXAMPLE 1

Cholesterol Suppresses Cellular TGF-β Responsiveness

Experimental Procedures
Materials $Na^{125}I$ (17 Ci/mg) and [methyl-$^3$H]thymidine (67 Ci/mmol) were purchased from ICN Radiochemicals (Irvine, Calif.). High molecular mass protein standards (myosin, 205 kDa; β-galactosidase, 116 kDa; phosphorylase, 97 kDa; bovine serum albumin, 66 kDa), DAPI, chloramine-T, bovine serum albumin (BSA), LDL, VLDL, HDL, fluvastatin (F), lovastatin (L), cholesterol (Chol), cholest-4-ene-3-one, disuccinimidyl suberate (DSS), nystatin (Nys), β-cyclodextrin (β-CD), hyaluronic acid (HA) and lipoprotein (a) (Lipo a) were obtained from Sigma (St. Louis, Mo.). 25-Hydroxycholesterol, 7-dehydrocholesterol (7-DHC), 7-ketocholestanol, 7-ketocholesterol (cholest-5-en-7-one), 7β, 8β-epoxy-cholesterol and 7β-hydroxycholesterol were obtained from Steraloids (Newport, R.I.). Oxidized 7-DHC (oxy-7DHC) was prepared by air drying a thin film of 7-DHC (initially dissolved in chloroform) at ambient room temperature, protected from exposure to light with aluminum foil, for one week. Reverse-phase HPLC revealed a mixture of polar products, but no remaining 7-DHC. Phospho-Smad2 (P-Smad2) antibody was obtained from Cell Signaling Technology, Inc. (Danvers, Mass.). TGF-$β_1$ was purchased from Austral Biologicals (San Ramon, Calif.). TGF-$β_2$ was purchased from R&D Systems (Minneapolis, Minn.). Rabbit polyclonal antibodies to caveolin-1, alk1, TβR-I (alk5) and TβR-II were obtained from Santa Cruz Biotechnology, Inc. (Santa Cruz, Calif.). The luciferase assay system was obtained from Promega (Madison, Wis.).

Cell Culture

Mink lung epithelial cells (Mv1Lu cells), MLECs-clone 32, which are Mv1Lu cells stably expressing the luciferase reporter gene driven by the PAI-1 promoter, bovine aorta endothelial cells (BAEC) and normal rat kidney fibroblasts (NRK cells) were maintained in DMEM or DMEM-F12 containing 10% fetal calf serum with or without bFGF.

$^{125}$I-TGF-$β_1$ Affinity Labeling

Cells grown on 6-well cluster dishes in DMEM or DMEM-F12 containing 10% fetal calf serum were treated with 50 μg/ml cholesterol or cholesterol derivatives, 5 or 50 μg protein/ml, LDL, HDL or VLDL, in serum-free medium at 37° C. for 1 hr or 1 μM fluvastatin or lovastatin in serum-free medium (volume=1 ml) at 37° C. for 18 hr. $^{125}$I-TGF-$β_1$ affinity labeling was then performed at 4° C. using the cross-linking agent disuccinimidyl substrate (DSS) as described previously. After cross-linking, cell lysates were analyzed by 7.5% SDS-PAGE and autoradiography or quantified by a PhosphoImager. For all experiments, cholesterol or cholesterol derivatives were prepared as the stock solution with a concentration of 25 mg/ml in ethanol. The final concentration of ethanol in the medium was 0.2% (by vol.). In all of the cell types used in the experiments, the type I receptor (TβR-I), which was cross-linked by $^{125}$I-TGF-$β_1$ using the bifunctional reagent DSS, was identified as alk5 as evidenced by immunoprecipitation of $^{125}$I-TGF-$β_1$-TβR-I complexes using specific antibodies to both alk1 and alk5.

Northern Blot Analysis

Cells grown to confluence on 12-well cluster dishes in DMEM containing 10% (by vol.) fetal calf serum were treated with several concentrations of cholesterol in serum-free DMEM (vol.=0.5 ml/well) at 37° C. for 1 hr. The cholesterol-treated cells were then incubated with 100 pM TGF-$β_1$ at 37° C. for 2 hr. The transcripts of PAI-1 and G3PDH (as control) in the cell lysates were analyzed by Northern blot analysis and quantified with a PhosphoImager (30) which yields a linearity from 9,000 to 100,000 arbitrary units of the transcript intensity.

Western Blot Analysis of Cultured Cells

Cells grown to near confluence on 12-well cluster dishes were treated with cholesterol or LDL in serum-free DMEM (vol.=0.5 ml/well) at 37° C. for 1 hr. The treated cells were further incubated with 50 or 100 pM TGF-$β_1$ at 37° C. for 30 min (for determining Smad2 phosphorylation) or for 2 hr (for determining TβR-II). Treated cells were lysed and cell lysates were analyzed by 7.5% SDS-PAGE and Western blot analysis using anti-Smad2, anti-P-Smad2, anti-caveolin-1, anti-TβR-I (alk5) or anti-TβR-II antibodies as described previously (30). The antigens on the blots were visualized by using horseradish peroxidase-conjugated anti-rabbit IgG antibody and the ECL system as described (30).

[Methyl-$^3$H]thymidine Incorporation

The growth of cholesterol-treated cells was determined by measurement of [methyl-$^3$H]thymidine incorporation into cellular DNA as described (30). Briefly, cells grown near confluence on 48-well clustered dishes were treated with several concentrations of cholesterol at 37° C. for 1 hr in serum-free DMEM. The final concentration of ethanol (the vehicle for cholesterol) in the medium was 0.2%. Treated cells were then incubated with 0.0625 pM or 0.125 pM of TGF-$\beta_1$ in DMEM containing 0.1% fetal calf serum at 37° C. for 18 hr. The [methyl-$^3$H]thymidine incorporation into cellular DNA was then determined by incubation of cells with [methyl-$^3$H]thymidine at 37° C. for 2 hr in DMEM containing 0.1% fetal calf serum. The optimal concentrations of TGF-$\beta_1$ to inhibit cell growth are in the range of 0.1 to 1 pM. Under the experimental conditions, cholesterol did not appear to affect cell viability.

$^{125}$I-TGF-$\beta_1$ Affinity Labeling and Western Blot Analysis of Aortic Endothelium from ApoE$^{-/-}$ and Wild-Type Mice ApoE$^{-/-}$ and wild-type mice (C57BL/6) were fed with high-cholesterol (2%) and normal diets for 3-4 weeks and then sacrificed. The plasma levels of cholesterol in ApoE$^{-/-}$ mice fed high-cholesterol and normal diets for 3-4 weeks were estimated to be 1,000-1,400 mg/dL and 500-700 mg/dL, respectively. The high-cholesterol diet did not significantly affect the plasma levels of wild-type mice (100-120 mg/dL). ApoE null mice fed a high-cholesterol diet exhibited typical atherosclerotic lesions in the aorta. ApoE null mice fed normal diet had no significant atherosclerotic lesions such as fatty streaks and plaques in the aorta as described previously. Aorta (~3 cm length) was removed and cut to open the vessel lumen and to expose the intima and then incubated with 100 pM $^{125}$I-TGF-$\beta_1$ in binding buffer containing 2 mg/ml bovine serum albumin. After 2.5 hr at 0° C., $^{125}$I-TGF-$\beta_1$-affinity labeling was performed using DSS as described previously. The aortas were then extensively washed and the intimal endothelium was scrapped off from the luminol surface of aorta. The aortic endothelium was then extracted with 0.1% Triton X-100. The Triton X-100 extracts were then analyzed by 7.5% SDS-PAGE and autoradiography or quantified by a PhosphoImager. Under the experimental conditions, $^{125}$I-TGF-$\beta_1$-affinity labeling occurred mainly in intimal endothelium as evidenced by the observation that the majority of $^{125}$I-TGF-$\beta_1$ radioactivity (>90%) in aortic endothelium could be removed by scrapping off intimal endothelium from the luminal surface of aorta using a razor blade. For Western blot analysis of aortic endothelium, aorta (~3 cm length) was cut to open the vessel lumen. Intimal endothelium was obtained by scrapping off the endothelium from the luminal surface of aorta using a razor blade and extracted with 0.1% Triton X-100. An equal protein amount (~50 μg) of Triton X-100 extracts was subjected to 7.5% SDS-PAGE followed by Western blot analysis using antibodies to P-Smad2 and Smad2 and quantified by chemilluminance and densitometry.

Luciferase Activity Assay and Indirect Immunofluorescent Staining

Mv1Lu cells stably expressing the luciferase reporter gene driven by the PAI-1 promoter (MLECs-Clone 32) (28) grown to near confluency on 12-well cluster dishes were treated with different concentrations of cholesterol or with and without 50 μg/ml cholesterol or 1 μM lovastatin at 37° C. for 1 hr or 16 hr, respectively. Treated cells were further incubated with 50 pM TGF-$\beta_1$ at 37° C. for 6-7 hr and lysed in 100 μl of lyses buffer (Promega). The cell lysates were then assayed using the luciferase kit from Promega. For indirect immunofluorescent staining, cells grown on cover glass were fixed in cold 100% methanol and then incubated with antibody to P-Smad2 overnight. The antigen was visualized by incubation with Rhodamine-conjugated goat antibody to rabbit IgG followed by immunofluorescence microscopy.

Separation of Lipid Raft and Non-Lipid Raft Microdomains of Plasma Membranes by Sucrose Density Gradient Ultracentrifugation Mv1Lu, CHO-K1, or NRK cells were grown to near confluence in 100-mm dishes (5-10×106 per dish). Cells were incubated with cholesterol (50 g/ml) at 37° C. for 1 hours and then incubated with TGF-$\beta_1$ (100 pM) for 1 hr. After two washes with ice-cold phosphate-buffered saline, cells were scraped into 0.85 ml of 500 mM sodium carbonate, pH 11.0. Homogenization was carried out with 10 strokes of a tight-fitting Dounce homogenizer followed by three 20-s bursts of ultrasonic disintegrator, (Soniprep 150; Fisher Scientific) to disrupt cellular membranes as described previously (32). The homogenates were adjusted to 45% sucrose by addition of 0.85 ml of 90% sucrose in 25 mM 2-(N-morpholino) ethanesulfonic acid, pH 6.5, 0.15 M NaCl (MBS), and placed at the bottom of an ultracentrifuge tube. A discontinuous sucrose gradient was generated by overlaying 1.7 ml of 35% sucrose and 1.7 ml of 5% sucrose in MBS on the top of the 45% sucrose solution and centrifuged at 39,000 rpm for 16-20 h in an SW55 TI rotor (Beckman Instruments, Palo Alto, Calif.). A light-scattering band was observed at the 3-35% sucrose interface. Ten 0.5-ml fractions were collected from the top of the tubes, and a portion of each fraction was analyzed by SDS-PAGE followed by Western blot analysis using antibodies to TβR-I and TβR-II and caveolin-1.

Burn Wound Model

Four pigs weighing 20-25 kg were anesthetized by intramuscular injection of ketamine (5 mg/kg), strenil (cazaporonum) (20 mg/kg) and atropine (5 mg/kg). Six uniform burn wounds (110° C., 30 sec) were then made symmetrically on the back of each pig using a modified soldering iron with a flat contact area of ~20 cm$^2$. The burn injury was equivalent to a full-thickness burn injury in humans and uniformly caused coagulation and necrosis of dermis. After wounding, IntraSite gels containing TGF-β antagonist and buffer vehicle (as control) were applied to the pig burn wounds. The burn wound received no topical gel treatment was also used as the other control. All wounds were dressed with paraffin gauze. TGF-β antagonist gel and control gel were applied to the wounds every two days for the first 10 days and twice a week for the next 30 days. All wounds were cleaned and measured prior to each application of the IntraSite gel.

Assessment of Wound Healing

Wound healing was assessed by evaluating the rates of wound re-epithelialization and contraction. The open wound area and the area enclosed by the normal hair bearing skin were measured using the macrophotography technique. The healing rate was monitored every two days for the first 10 days and twice a week for 30 more days. Wound re-epithelialization or contraction as a percent of the original wound size was calculated as described previously.

Statistical Analysis

The data are expressed as the mean±S.D. from 4 pigs and 3 rabbits in each type of wound. Statistical analysis of wound contraction and re-epithelialization was performed by the Student's t test.

Measurement of Scar

The volumes of scar were estimated by multiplying their thickness by the size of the scar on post-burn day 41 in pigs and on post-excision day 10 in rabbits.

Assessment of Wound Healing

Wound healing was assessed by evaluating the rates of wound re-epithelialization and contraction. The open wound area and the area enclosed by the normal hair bearing skin were measured using the macrophotography technique. The healing rate was monitored every two days for the first 10 days and twice a week for 30 more days. Wound re-epithelialization or contraction as a percent of the original wound size was calculated as described previously.

Hair Growth Assay

Hair at the back of female mice (C57BL/6, 6-8 weeks old, were removed by using Nair® lotion hair remover. Lotions containing 0.025 and 0.00625% cholesterol and vehicle only were topically applied onto the area where the hair was removed. On the first day and every other day, photographs were taken prior to administration of the lotions. On day 18, the re-grown hair was shaved and weighed.

Statistical Analysis

The values represented the mean±S.D. Two-tailed unpaired Student's t test was used to determine the significance of differences between groups. $p<0.05$ was considered significant.

Results

Treatments of Cells with Cholesterol and Statins Suppress and Enhance TGF-β Responsiveness, Respectively.

Figure 1:
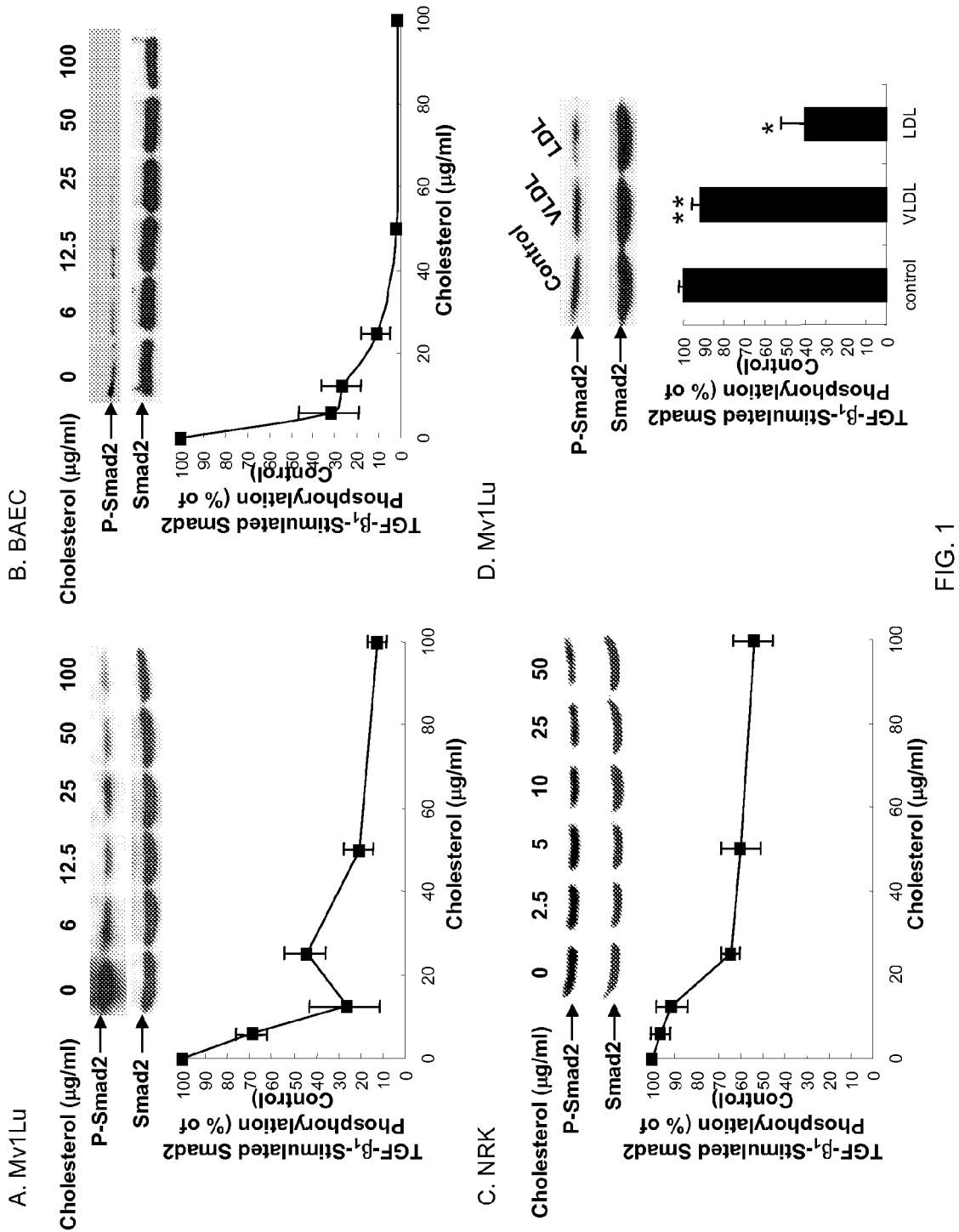
FIG. 1: Effects of cholesterol and LDL on TGF-β-stimulated Smad2 phosphorylation (A, B, C, D) and nuclear translocations (E) in Mv1Lu, BAEC and NRK cells.
Figure 1:
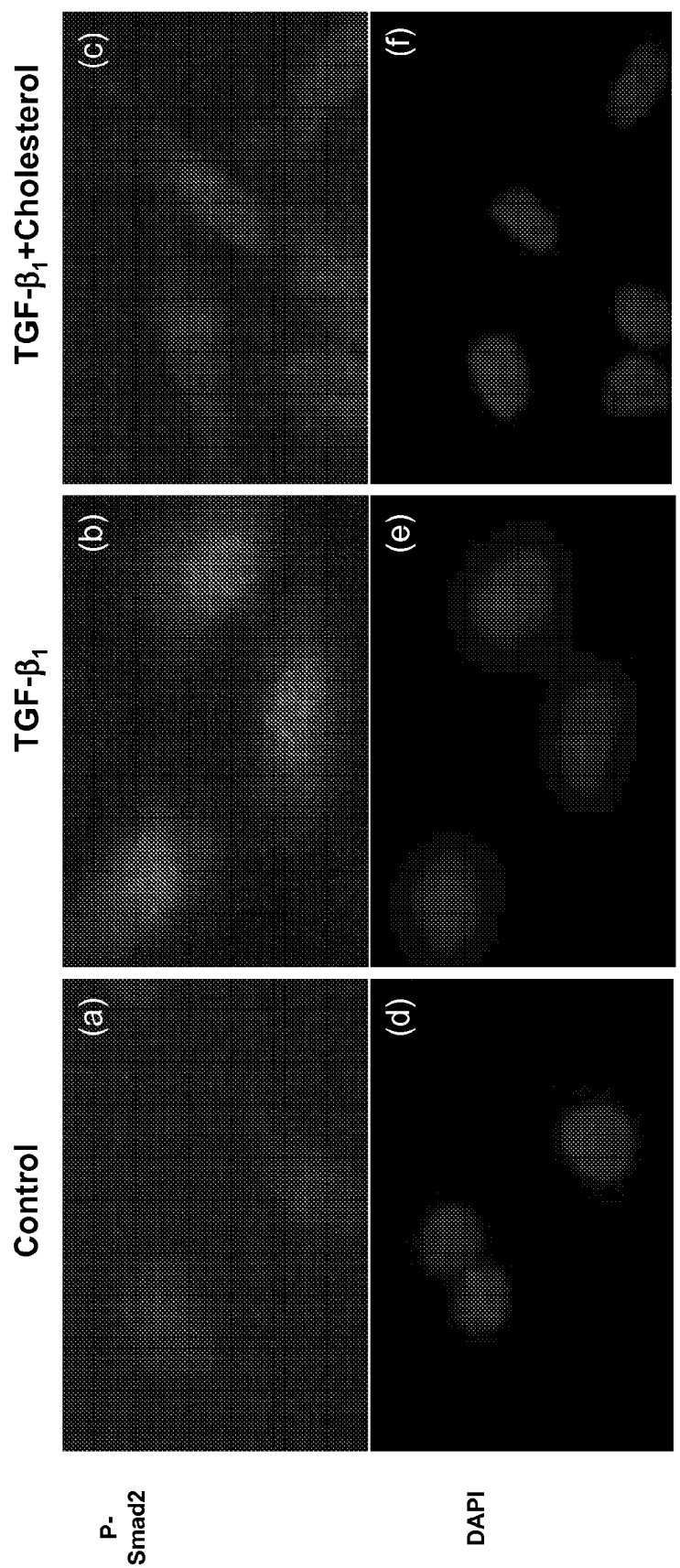

It has been reported that TGF-β responsiveness is determined by TGF-β partitioning between lipid raft/caveolae-mediated and clathrin-mediated endocytosis. Lipid-raft/caveolae-mediated endocytosis facilitates TGF-β degradation and thus suppresses TGF-β responsiveness. Clathrin-mediated endocytosis results in endosomal signaling, promoting TGF-β responsiveness. Since cholesterol is an important component of lipid rafts/caveolae, the treatment of cells with cholesterol may suppress TGF-β-induced signaling by promoting formation of or stabilizing lipid rafts/caveolae. To test this possibility, we determined the effect of cholesterol treatment on Smad2 phosphorylation and nuclear translocation, both of which are key signaling events, leading to TGF-β responsiveness. Mink lung epithelial cells (Mv1Lu cells, a standard model system for investigating TGF-β responsiveness), bovine aorta endothelial cells (BAEC) and normal rat kidney cells (NRK cells) were treated with increasing concentrations of cholesterol at 37° C. for 1 hr and then further incubated with 50 pM TGF-$β_1$ at 37° C. for 0.5 hr. Phosphorylated Smad2 (P-Smad2) in the cell lysates was determined by 7.5% SDS-PAGE followed by Western blot analysis using anti-P-Smad2 antibody and enhanced chemiluminescence, and quantified by densitometry. As shown in FIG. 1, cholesterol effectively suppressed Smad2 phosphorylation stimulated by TGF-$β_1$ in a concentration-dependent manner. Cholesterol treatment appreciably suppressed Smad2 phosphorylation at concentrations of 6 or 10 µg/ml. At 25 µg/ml, cholesterol suppressed Smad2 phosphorylation by 55%, 90%, and 40% in Mv1Lu, BAEC, and NRK cells, respectively (FIGS. 1A, B and C). Since cholesterol is mainly present as lipoprotein complexes (e.g. LDL and VLDL) in plasma, we determined the effects of LDL and VLDL on Smad 2 phosphorylation in Mv1Lu cells. As shown in FIG. 1D, LDL (50 µg protein/ml) treatment suppressed Smad2 phosphorylation by 60% in Mv1Lu cells and VLDL (5 µg/ml) slightly suppressed Smad2 phosphorylation in these cells. At 50 µg protein/ml, VLDL suppressed Smad2 phosphorylation by 55±5% (n=4) in Mv1Lu cells (data not shown). The concentration (50 ug/ml) of LDL used in the experiment was chosen because it caused inhibition of Smad2 phosphorylation by 60% which was similar to that induced by 25 ug/ml cholesterol. To determine the effect of cholesterol on Smad2 nuclear translocation, Mv1Lu cells were treated with 50 µg/ml cholesterol at 37° C. for 1 hr and then further incubated with and without 50 pM TGF-$β_1$ at 37° C. for 30 min. These cells were subjected to immunofluorescent staining using anti-P-Smad2 antibody and nuclear DAPI (4',6-diamidine-2-phenylindole dihydrochloride) staining. As shown in FIG. 1E, cholesterol suppressed Smad2 nuclear translocation (c versus b). Taken together, these results suggest that cholesterol treatment suppresses TGF-$β_1$-induced signaling.

One important activity of TGF-β is the transcriptional activation of genes coding for extracellular matrix (ECM) proteins and their regulatory proteins such as plasminogen activator inhibitor-1 (PAI-1). This transcriptional activation is mediated by the Smad signaling pathway. To define the effect of cholesterol on TGF-β responsiveness, we determined the effect of cholesterol (50 µg/ml) on PAI-1 expression in cells stimulated with several concentrations of TGF-$β_1$ by Northern blot analysis and quantified using a PhosphoImager. PAI-1 expression is commonly used to determine TGF-β responsiveness in many cell types. As shown in FIGS. 2A, B and C, treatment with 50 µg/ml cholesterol effectively suppressed PAI-1 expression in Mv1Lu (FIG. 2A), BAEC (FIG. 2B) and NRK (FIG. 2C) cells stimulated by several concentrations of TGF-$β_1$, ranging from 2 to 100 pM. Cholesterol suppressed TGF-$β_1$-stimulated PAI-1 expression by 65-70%, 50-80% and 60-65% in Mv1Lu, BAEC and NRK cells, respectively.

The above results suggest that cholesterol suppresses TGF-$β_1$-stimulated PAI-1 expression in these various cell types. To define the physiological relevance of the cholesterol effect, we examined the effect of LDL (a major cholesterol vehicle in blood) or fluvastatin/lovastatin (potent HMG-CoA reductase inhibitors commonly employed as cholesterol-lowering drugs) on PAI-1 expression in Mv1Lu cells stimulated by TGF-$β_1$. Mv1Lu cells were pretreated with LDL (50 µg protein/ml) or cholesterol (50 µg/ml) at 37° C. for 1 hr, or with fluvastatin or lovastatin (1 µM) at 37° C. for 16 hr, and PAI-1 expression in these TGF-$β_1$-stimulated cells was determined by Northern blot analysis and quantified using a PhosphoImager. At 1 uM, fluvastatin or lovastatin inhibited cholesterol synthesis by >90% as described previously. As shown in FIG. 2D, LDL and cholesterol suppressed TGF-$β_1$-induced PAI-1 expression by 50-60% in these cells (FIGS. 2Da and 2Db). The LDL and cholesterol effects were abolished in the presence of 25 µg/ml nystatin (a cholesterol-sequestering compound; data not shown). Conversely, fluvastatin and lovastatin enhanced PAI-1 expression stimulated with 50 pM TGF-$β_1$ in Mv1Lu cells (FIG. 2E). Fluvastatin appeared to be more potent than lovastatin on a molar basis. Fluvastatin (1 µM) enhanced PAI-1 expression stimulated with 10 pM TGF-$β_1$ by 3 fold whereas lovastatin (1 µM) did not enhance PAI-1 expression stimulated with 10 pM TGF-$β_1$ (FIG. 2Eb). However, lovastatin was capable of enhancing PAI-1 expression stimulated with 50 pM TGF-$β_1$ by 3 fold in these cells (FIG. 2Eb). Fluvastatin enhanced PAI-1 expression stimulated by 50 µM TGF-$β_1$ in a concentration-dependent manner (FIG. 2Fa) with an $EC_{50}$ of 0.5 µM (FIG. 2Fb). These results suggest that the cholesterol effect is physiologically relevant, because LDL is a major cholesterol carrier in the blood, and fluvastatin and lovastatin have been used to treat human patients with hypercholesterolemia. The effect of treatment with cholesterol or lovastatin on TGF-β responsiveness was further characterized using Mv1Lu cells stably expressing a luciferase reporter driven by the PAI-1 gene promoter. As shown in FIG. 2G, treatment of cells with 50 μg/ml cholesterol suppressed luciferase activity stimulated with 50 pM TGF-$\beta_1$ by 40%, (FIG. 2Ga) while 1 μM lovastatin enhanced the TGF-$\beta_1$-stimulated luciferase activity by 1.7 fold (FIG. 2Gb). The stimulatory effect of lovastatin on TGF-β-stimulated luciferase activity was abolished by treatment of Mv1Lu cells with cholesterol (25 ug/ml) for 1 hr prior to TGF-β stimulation. The luciferase activity (2314±120 A.U) in cells treated with cholesterol, lovastatin and TGF-$\beta_1$ is almost identical to that of cells treated with TGF-$\beta_1$ alone. Cholesterol alone did not alter the TGF-β-stimulated luciferase activity under the experimental conditions. This suggests that the lovastatin effect is mainly through its inhibition of cholesterol synthesis.

Another prominent biological activity of TGF-β is growth inhibition of many different cell types. If cholesterol suppresses TGF-β responsiveness, it should antagonize TGF-$\beta_1$ growth inhibitory activity. To test this, Mv1Lu cells were treated with several concentrations (as indicated) of cholesterol at 37° C. for 1 hr and then further incubated with 0.0625 or 0.125 pM TGF-$\beta_1$ at 37° C. for 18 hr. DNA synthesis was then determined by measurement of [$^3$H-methyl]thymidine incorporation into cellular DNA (FIG. 2Ha). It is important to note that the optimal concentrations of TGF-$\beta_1$ for growth inhibition are much lower than those for transcription activation. The former are in the range of 0.1 to 2 pM whereas the latter are in the range of 10 to 100 pM. As shown in FIG. 2Ha, TGF-$\beta_1$ at 0.0625 and 0.125 pM inhibited DNA synthesis by ~30 and 40%, respectively. Treatment with increasing concentrations of cholesterol correspondingly reversed DNA synthesis inhibition induced by TGF-$\beta_1$. Cholesterol at 6 and 8 μg/ml alone inhibited DNA synthesis in Mv1Lu cells. It was estimated that cholesterol (8 μg/ml) almost completely reversed DNA synthesis inhibition induced by 0.0625 and 0.125 pM TGF-$\beta_1$ (FIG. 2Hb). Together with the results shown above, this finding suggests that cholesterol is a potent TGF-$\beta_1$ antagonist.

Cholesterol and Statins Suppress and Enhance TGF-β Responsiveness by Decreasing and Increasing the Ratio of TGF-$\beta_1$ Binding to TβR-II and TβR-I on the Cell Surface, Respectively.

The ratio of TGF-$\beta_1$ binding to TβR-II and TβR-I has been shown to be positively correlated with TGF-β responsiveness in several cell systems. We recently reported that the ratio of TGF-$\beta_1$ binding to type II and type I TGF-β receptors in TGF-β receptor complexes on the cell surface is a signal determining TGF-β partitioning between lipid raft/caveolae- and clathrin-mediated endocytosis and resultant TGF-β responsiveness. When the ratio increases, more receptor-bound TGF-$\beta_1$ (as Complex I, which contains more TβR-II than TβR-I (alk5) and exists in non-lipid raft microdomains) undergoes clathrin-mediated endocytosis and generates signaling in endosomes, leading to TGF-β responsiveness; when the ratio decreases, more receptor-bound TGF-$\beta_1$ (as Complex II, which contains more TβR-I than TβR-II and exists in lipid rafts/caveolae) undergoes lipid raft/caveolae-mediated endocytosis and rapid degradation, resulting in suppressing TGF-β responsiveness. To determine if cholesterol suppresses TGF-β responsiveness by decreasing the ratio of TGF-$\beta_1$ binding to TβR-II and TβR-I, we first determined the time course of the effect of cholesterol treatment on the ratio of $^{125}$I-TGF-$\beta_1$ binding to TβR-II and TβR-I in Mv1Lu cells. These cells were treated with 50 μg/ml cholesterol at 37° C. for several time periods. $^{125}$I-TGF-$\beta_1$ binding to TGF-β receptors was then determined by affinity labeling using the bifunctional cross-linking agent DSS (disuccinimidyl suberate) followed by 7.5% SDS-PAGE and autoradiography or quantified with a PhosphoImager. As shown in FIG. 3A, treatment of Mv1Lu cells with 50 μg/ml cholesterol increased binding of $^{125}$I-TGF-$\beta_1$ to TβR-I in a time-dependent manner but had little effect on $^{125}$I-TGF-$\beta_1$ binding to TβR-II. Cholesterol increased $^{125}$I-TGF-$\beta_1$ binding to TβR-I by ~1.5 fold after a 60-min or 120-min incubation whereas it did not affect $^{125}$I-TGF-$\beta_1$ binding to TβR-II after the same time incubation. Cholesterol treatment for 60 min or 120 min appeared to decrease the ratio of TβR-II/TβR-I from 0.37 (treatment without cholesterol) to 0.18 (FIG. 3Ab). Treatment with cholesterol (50 μg/ml) in the experimental periods did not affect the protein levels of TβR-I and TβR-II based on Western blot analysis (data not shown). This suggests that cholesterol treatment may suppress TGF-β responsiveness in Mv1Lu cells by increasing formation of Complex II, facilitating lipid-raft-mediated endocytosis and rapid degradation of receptor-bound TGF-β. We then performed analysis of the effect of cholesterol treatment on TGF-$\beta_1$ binding to TβR-I and TβR-II in several cell types. Mv1Lu, BAEC, and NRK cells were treated for 1 hr with increasing concentrations of cholesterol in the presence and absence of 0.2% β-cyclodextrin (β-CD, which forms water-soluble complexes with cholesterol) at 37° C. The binding of TGF-$\beta_1$ to TβR-I and TβR-II in these cells was then determined by $^{125}$I-TGF-$\beta_1$ affinity labeling at 0° C. As shown in FIGS. 3B, D and E, cholesterol treatment greatly increased the binding of $^{125}$I-TGF-$\beta_1$ to TβR-I but did not significant alter the binding of $^{125}$I-TGF-$\beta_1$ to TβR-II in these three cell types. At 50 μg/ml, cholesterol increased $^{125}$I-TGF-$\beta_1$ binding to TβR-I by ~2.5 fold, ~2.5 fold and ~5.7 fold in Mv1Lu, BAEC, and NRK cells, respectively. Thus, cholesterol (50 μg/ml) decreased the ratio of TβR-II/TβR-I from 0.42 to 0.20, 3.5 to 1.4, and 2.0 to 0.35 in Mv1Lu, BAEC, and NRK cells, respectively. In the presence of β-CD, higher concentrations of cholesterol were required for maximally increasing $^{125}$I-TGF-$\beta_1$ binding to TβR-I in Mv1Lu cells (FIG. 3C). At 125 μg/ml in the presence of 0.2% β-CD, cholesterol increased $^{125}$I-TGF-$\beta_1$ binding to TβR-I by ~3 fold with little effect on $^{125}$I-TGF-$\beta_1$ binding to TβR-II in Mv1Lu cells (FIG. 3C). These results suggest that cholesterol may suppress TGF-β responsiveness by decreasing the ratio of TGF-$\beta_1$ binding to TβR-II and TβR-I in TGF-β receptor complexes on the cell surface (as Complex II) in these cell types.

To determine if cholesterol treatment affects the affinity of TGF-$\beta_1$ binding to TβR-I and TβR-II, Mv1Lu cells were treated with 50 μg/ml cholesterol at 37° C. for 1 hr and then incubated with increasing concentrations of $^{125}$I-TGF-$\beta_1$ at 0° C. for 2.5 hr. $^{125}$I-TGF-$\beta_1$ affinity labeling was performed. $^{125}$I-TGF-$\beta_1$ affinity-labeled TGF-β receptors were then analyzed by 7.5% SDS-PAGE and autoradiography (FIG. 3Fa and 3Fb, top) or quantified with a PhosphoImager (FIGS. 3Fa and 3Fb, bottom). Cholesterol (50 μg/ml) appeared to increase $^{125}$I-TGF-$\beta_1$ (125 pM) binding to TβR-I by ~2 fold (from ~350 to ~700×10$^3$ A.U.) but did not increase $^{125}$I-TGF-$\beta_1$ binding to TβR-II (from ~180 to ~120×10$^{-3}$ A.U.) (FIG. 3Fb, bottom versus FIG. 3Fa, bottom). The half-maximum concentrations of $^{125}$I-TGF-$\beta_1$ binding to TβR-I and TβR-II were 50-80 pM in Mv1Lu cells treated with and without cholesterol. The half-maximum concentration, 50-80 pM, was identical to the apparent $K_d$ of TGF-$\beta_1$ binding to the TGF-β receptors. These results suggest that cholesterol treatment increases TGF-$\beta_1$ binding to TβR-I and thus decreases the ratio of TGF-$\beta_1$ binding to TβR-II and TβR-I but does not alter the affinities of TGF-$\beta_1$ binding to both TβR-I and TβR-II.

To further define the physiological significance of the cholesterol effect on TGF-$\beta_1$ binding to TβR-I, we determined the effect of pretreatment at 37° C. for 1 hr with cholesterol-containing lipoproteins (LDL, VLDL and HDL), cholesterol-binding compounds nystatin and β-CD, 4-cholesten-3-one (a cholesterol derivative) and cholesterol, alone or in combination, on $^{125}$I-TGF-β$_1$ binding to TGF-β receptors (as determined by $^{125}$I-TGF-β$_1$ affinity labeling at 0° C. in the absence of the agents) in Mv1Lu cells. As shown in FIG. 4, LDL and VLDL increased $^{125}$I-TGF-β$_1$ binding to TβR-I but not TβR-II (FIG. 4A, lanes 2 and 5 versus lane 1), and thus decreased the ratio of TβR-II/TβR-I from 0.46 to 0.18 and 0.25, respectively. HDL slightly decreased $^{125}$I-TGF-β$_1$ binding to TβR-I (FIG. 4A, lane 3 versus lane 1) and increased the ratio of TβR-II/TβR-I from 0.46 to 0.56. Lipoprotein (a), an atherogenic lipoprotein, did not significantly affect $^{125}$I-TGF-β$_1$ binding to TβR-I or TβR-II (FIG. 4A, lane 4 versus lane 1). The LDL- or cholesterol-induced increase of $^{125}$I-TGF-β$_1$ binding to TβR-I was abolished in the presence of β-CD, nystatin, or 4-cholesten-3-one, (FIG. 4B, lanes 3, 5 and 6 versus lane 2 and FIG. 4C, lanes 5 and 6 versus lane 4). For example, the ratio of TβR-II/TβR-I in cells treated with both cholesterol and β-CD or nystatin was similar to that of cells treated with β-CD or nystatin alone (FIG. 4C, lanes 5 and 6 versus lanes 2 and 3). These agents, alone or together, did not affect $^{125}$I-TGF-β$_1$ affinity labeling at 0° C. without preincubation with cells at 37° C. for 1 hr, suggesting that these agents do not directly affect $^{125}$I-TGF-β$_1$ binding to TβR-I and TβR-II under the experimental conditions (data not shown). These results suggest that LDL and VLDL may suppress TGF-β responsiveness by decreasing the ratio of TβR-II/TβR-I (or increasing formation of Complex II) and thus facilitating lipid-raft-mediated endocytosis and rapid degradation of receptor-bound TGF-β$_1$. These results also suggest that the LDL-induced increase of $^{125}$I-TGF-β$_1$ binding to TβR-I and the resulting decrease in the ratio of TβR-II/TβR-I is mediated by cholesterol per se, rather than by the protein or other lipid components of LDL.

Since statins are cholesterol-lowering drugs, we reasoned that pretreatment of cells with statins (1 μM; at 37° C. for 16 hr) should reduce the cholesterol content in the plasma membrane and thereby decrease TGF-β$_1$ binding to TβR-I and increase the ratio of TGF-β$_1$ binding to TβR-II and TβR-I (i.e., the converse of the cholesterol-induced increase of TGF-β$_1$ binding to TβR-I). As shown in FIGS. 4D, E and F, treatment with fluvastatin (F) or lovastatin (L) decreased $^{125}$I-TGF-β$_1$ binding to TβR-I (FIGS. 4D, E, and F, lanes 2 and 3 versus lane 1) and thus increased the ratio of TβR-II/TβR-I from 0.12 to 0.19 or 0.18, 0.88 to 1.3 or 1.18 and 2.47 to 2.91 or 2.6 in CHO-K1 cells (Chinese hamster ovary cells), in Mv1Lu cells, and in BAEC cells, respectively. The statin effect was abolished by the addition of exogenous cholesterol (FIGS. 4D, E and F, lanes 5 and 6 versus lanes 2 and 3), suggesting that the statin effect is due to its cholesterol-lowering properties. These results suggest that statin treatment may enhance TGF-β responsiveness by increasing the ratio of TβR-II/TβR-I and thus facilitating clathrin-mediated endocytosis and endosomal signaling.

To define the specificity of the cholesterol effect, we determined the effects of cholesterol analogs and derivatives on $^{125}$I-TGF-β$_1$ binding to TβR-I and TβR-II in Mv1Lu cells. These cells were treated with 50 μg/ml of cholesterol or related oxysterol derivatives (25-hydroxycholesterol, 7-dehydrocholesterol (7-DHC), oxidized 7-DHC (oxy-7-DHC), cholest-5-en-7-one, 7-ketocholesterol, 7β,8β-epoxycholestanol, and 7β-hydroxycholesterol) at 37° C. for 1 hr. $^{125}$I-TGF-β$_1$ binding to TGF-β receptors was then determined by affinity labeling. Under the experimental conditions, treatment of Mv1Lu cells with cholesterol analogs and derivatives did not affect cell viability. As shown in FIG. 4G, cholesterol was the most potent of these compounds in increasing $^{125}$I-TGF-β$_1$ binding to TβR-I and decreasing the ratio of TGF-β$_1$ binding to TβR-II and TβR-I (lane 2) from 0.62 to 0.29 (lane 2 versus lane 1). Curiously, a mixture of oxysterols produced by exhaustive air oxidation of 7-DHC in darkness ("oxy-7DHC") (lane 5) appeared to be nearly as potent as cholesterol in this regard, notably much more so than an equivalent amount of pure 7-DHC.

Cholesterol and Statins Increase Localization of TβR-I and TβR-II in Lipid Rafts/Caveolae and Non-Lipid Raft Microdomains of the Plasma Membrane, Respectively.

TGF-β$_1$ partitioning between clathrin- and lipid raft/caveolae-mediated endocytosis has been shown to determine TGF-β responsiveness. Lipid raft/caveolae-mediated endocytosis of receptor-bound TGF-β results in rapid degradation of TGF-β$_1$ and suppression of TGF-β responsiveness. Conversely, clathrin-mediated endocytosis of receptor-bound TGF-β leads to endosomal signaling and TGF-β responsiveness. The signal which determines TGF-β$_1$ partitioning between lipid raft/caveolae- and clathrin-mediated endocytosis and resultant TGF-β responsiveness appears to be the ratio of TGF-β$_1$ binding to TβR-II and TβR-I. Since cholesterol treatment greatly increases TGF-β$_1$ binding to TβR-I and formation of Complex II which exists in lipid rafts/caveolae of the plasma membrane and mainly utilizes the lipid raft/caveolae endocytosis pathway, it should also result in enhanced lipid raft/caveolae-mediated endocytosis of receptor-bound TGF-β$_1$ and suppressed TGF-β responsiveness. To test this, we analyzed the lipid raft/caveolae and non-lipid raft localization of TβR-I and TβR-II in the plasma membrane of cells treated with or without cholesterol (50 μg/ml) using sucrose density gradient ultracentrifugation analysis. As shown in FIGS. 5A and B, TβR-II was mainly localized in non-lipid raft fractions (fractions 7 and 8, which contain the transferrin receptor-1) of Mv1Lu, and NRK cells before treatment with cholesterol whereas TβR-I was present in both the non-lipid raft and lipid raft/caveolae (fractions 4 and 5, which contain caveolin-1) fractions. TβR-I was not analyzed in Mv1Lu cells due to the poor reactivity of the anti-TβR-I antibody used in the experiment to mink TβR-I. After treatment with cholesterol, both TβR-I and TβR-II were found to be enriched in the lipid raft/caveolae fractions (fractions 4 and 5) of the plasma membrane in Mv1Lu cells compared to the same fractions before cholesterol treatment (FIGS. 5A, B, C and D). Treatment with cholesterol alone did not affect the total amount of TβR-II protein in these cells. Mv1Lu cells used in the experiments shown in FIG. 5A and FIG. 5C were from different passages of the cultured cells and exhibited different patterns of TβR-II distribution in the sucrose density gradient fractions. Addition of TGF-β$_1$ to the medium (for 1 hr) induced degradation of TβR-II in lipid raft/caveolae of plasma membranes in Mv1Lu and NRK cells (FIGS. 5C and D, fractions 4 and 5). TGF-β$_1$ did not affect the synthesis of TβR-II in these cells as determined by pulse-labeling of these cells with $^{35}$S-methionine followed by immunoprecipitation and fluorography as described previously. Co-treatment with cholesterol further enhanced TGF-β$_1$-induced degradation of TβR-II in non-lipid raft microdomains via lipid rafts/caveolae (FIGS. 5C and D, fractions ⅞). Cholesterol appeared to enhance TGF-β$_1$-induced degradation of TβR-II in non-lipid raft microdomains by shifting TβR-II localization from non-lipid raft microdomains (fractions ⅞) to lipid rafts/caveolae (fractions ⅘) (FIGS. 5C and D). Cholesterol enhanced TGF-β$_1$-induced degradation of TβR-II in a concentration-dependent manner (FIG. 5Ea and FIG. 5Ec). Cholesterol (10 μg/ml) and LDL (15 μg protein/ml) enhanced TGF-β$_1$-induced degradation of TβR-II by 70% (FIG. 5Eb and FIG. 5Ed). Treatment with cholesterol (10 µg/ml) or LDL (15 µg protein/ml) alone did not induce TβR-II degradation (FIGS. 5Eb and 5Ed). The cholesterol-enhanced TGF-$β_1$-induced degradation of TβR-II was abolished by β-CD, a cholesterol binding compound (FIG. 5Eb). Cholesterol binding compounds (e.g. nystatin) have been shown to inhibit lipid-raft-mediated degradation of TGF-β receptors. These results suggest that cholesterol or LDL treatment increases lipid raft/caveolae localization and subsequent degradation of TβR-I and TβR-II, resulting in suppression of TGF-β responsiveness and that the cholesterol-enhanced TGF-$β_1$-induced degradation of TβR-II is effectively prevented by co-treatment of cells with β-CD.

To define the role of endogenous cholesterol in determining the localization of TβR-II in plasma membrane microdomains, Mv1Lu cells were treated with 1 µM lovastatin/1 µM fluvastatin or 25 µg/ml nystatin/50 µg/ml cholesterol at 37° C. for 16 hr or 1 hr, respectively. The plasma membrane microdomain localization of TβR-II was determined by sucrose density gradient ultracentrifugation followed by Western blot analysis. As shown in FIG. 5F, treatment with lovastatin, fluvastatin or nystatin increased the localization of TβR-II in non-lipid raft microdomains (fraction 7) whereas treatment with cholesterol increased the localization of TβR-II in lipid rafts/caveolae (fraction 4). The fluvastatin-induced increased localization of TβR-II in non-lipid raft microdomains appeared to suppress degradation of TβR-II induced by TGF-$β_1$ (FIG. 5G). It is important to note that treatment of Mv1Lu cells with fluvastatin at 37° C. for 16 hr increases the total amount of TβR-II by ~1.5 fold when compared with those of cholesterol-treated and control cells (FIGS. 5F and G). This could be due to decreased degradation and/or increased biosynthesis of TβR-II in cells treated with fluvastatin. Taken together with the results shown in FIGS. 2E and F, these results suggest that treatment of cells with the statins increases localization of TβR-II in non-lipid raft microdomains and presumably increases endosomal signaling, resulting in enhancing TGF-β responsiveness.

Cholesterol Promotes Wound Healing and Reduces Scarring in a Standard Pig Skin Burn Injury Model.

Herein we present several lines of evidence indicating that cholesterol is a novel TGF-β antagonist. These include: 1) Cholesterol treatment of cells suppresses TGF-β-induced cellular responsiveness including TGF-β induced Smad2 phosphorylation and nuclear translocation and TGF-β-induced expression of plasminogen activator inhibitor-1 (PAI-1). PAI-1 gene expression has commonly been used as an indicator of TGF-β-induced cellular responsiveness and PAI-1 is involved in inhibiting degradation of ECM proteins. And 2) Cholesterol treatment reverses TGF-β-induced growth inhibition in Mv1Lu cells. Since TGF-β negatively regulates normal wound healing and mediates skin fibrosis and scarring, we decided to test the effect of cholesterol on wound healing and scar formation in a pig skin burn injury model. Six thermal burns (110° C., 30 sec.; ~20 cm$^2$, three on each side) were created on the back on each pig (20 kg, female). After wounding, two lesions were treated with a thin-layer of gel containing 0.025% cholesterol; two received gel containing 0.006% cholesterol and two received gel containing vehicle only. Cholesterol and cholesterol gels were applied every 2 days for the first 10 days and twice a week for the nest 30 days at which time re-epithelialization was measured and photographed. As shown in FIG. 6, cholesterol enhanced healing, promoted wound healing and reduced scarring in a dose-dependent manner. On post-burn day 38, wounds treated with 0.025 and 0.00625% cholesterol exhibited complete and almost complete wound closure, respectively. By contrast, the wound treated with vehicle only exhibited a significant size of open wound. Less scarring was seen in wounds treated with cholesterol. The volumes of the scar tissue in wound treated with 0.025% and 0.00625% cholesterol were 0.01 and 0.20±0.04 cm$^3$, respectively. The volume of the scar tissue in wounds treated with vehicle only was 0.45±0.03 cm$^3$. It is important to note that the surface of wounds treated with 0.025% cholesterol appeared to be very smooth without apparent scar. These results suggest that topical administration of cholesterol is effective in promoting wound healing and reducing scarring in a standard pig skin injury model.

Cholesterol Promotes Hair Growth in a Mouse Model.

The hair growth cycle is coordinated with complex processes that are dependent on the interactions of epithelial and dermal components (follicle keratinocytes and dermal papilla cells). The hair growth cycle includes two major phases, growing phase (anagen) and regression phase (catagen). The length and size of hair are dependent on the anagen term in the hair cycle. TGF-β is a recognized key inducer of catagen in human hair follicles. TGF-β produced from dermal cells inhibits growth, and causes apoptosis of hair follicle cells, resulting in initiation of catagen. Androgen induces catagen by up-regulating TGF-β expression in dermal papilla cells. Because of negative role of TGF-β in hair growth, TGF-β has been suggested to be an excellent target for innovative treatment of alopecia. To test the effect of cholesterol, which is a novel TGF-β antagonist on hair growth, we treated mice topically with the lotion containing 0.025% cholesterol and vehicle only every two days on the back where the hair was removed by lotion hair remover. The photographs were taken on days 0, 10 and 18. As shown in FIG. 7, cholesterol treatment augmented hair growth when compared with that treated with vehicle only. On day 10, the hair started to grow (as indicated by appearance of dark color) in treated mice (FIG. 7e) whereas the hair growth was barely detected in vehicle-treated mice (FIG. 7b). On day 18, mice treated with cholesterol exhibited fully grown hair (FIG. 7f). In contrast, mice treated with vehicle only exhibited partial hair growth (in ~80% of the area) (FIG. 7c) with an average length of ~40-50% of that seen in mice treated with cholesterol. These results suggest that cholesterol is effective in promoting hair growth when topically applied.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims. It should also be understood that the embodiments described herein are not mutually exclusive and that features from the various embodiments may be combined in whole or in part in accordance with the invention.

What is claimed is:

1. A method for treating dermal wounds in a subject in need of treatment, the method comprising administering to the subject a composition comprising a therapeutically effective amount of a TGF β inhibitor, the TGF β inhibitor consisting of a cholesterol derivative having the Formula II:

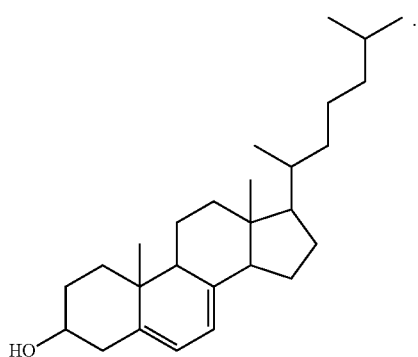

Formula II

2. The method of claim 1 wherein the administering step is topical administration to a dermal wound expressing TGF-β.

3. The method of claim 1 wherein the administering step is transdermal administration to a dermal wound expressing TGF-β.

4. The method of claim 1 wherein the administering step is intradermal administration to a dermal wound expressing TGF-β.

5. The method of claim 1 wherein the composition further comprises at least one ceramide.

6. The method of claim 5 wherein the at least one ceramide is ω-esterified ceramides, acylceramides, cerebrosides, co-esterified cerebrosides, or acylglycosyl sphingolipids.

7. The method of claim 1 wherein the composition is administered directly to the dermal wound.

8. The method of claim 1 wherein the composition further comprises a penetration enhancer.

* * * * *